US010706476B2

(12) United States Patent
Niemeyer

(10) Patent No.: US 10,706,476 B2
(45) Date of Patent: Jul. 7, 2020

(54) COMPUTER IMPLEMENTED METHODS AND SYSTEMS FOR BUNDLED PAYMENT ADJUDICATION

(71) Applicant: NOVERA, LLC, O'Fallon, MO (US)

(72) Inventor: Mark Niemeyer, O'Fallon, MO (US)

(73) Assignee: Novera, LLC, O'Fallon, MO (US)

( * ) Notice: Subject to any disclaimer, the term of this patent is extended or adjusted under 35 U.S.C. 154(b) by 57 days.

(21) Appl. No.: 16/234,405

(22) Filed: Dec. 27, 2018

(65) Prior Publication Data

US 2019/0318431 A1   Oct. 17, 2019

Related U.S. Application Data

(60) Provisional application No. 62/657,752, filed on Apr. 14, 2018.

(51) Int. Cl.
| | |
|---|---|
| *G16H 10/60* | (2018.01) |
| *G06Q 40/08* | (2012.01) |
| *G06Q 30/04* | (2012.01) |
| *G06F 16/23* | (2019.01) |

(52) U.S. Cl.
CPC ......... *G06Q 40/08* (2013.01); *G06F 16/2365* (2019.01); *G06Q 30/04* (2013.01); *G16H 10/60* (2018.01)

(58) Field of Classification Search
USPC ....................................................... 705/2, 3
See application file for complete search history.

(56) References Cited

U.S. PATENT DOCUMENTS

| | | |
|---|---|---|
| 8,165,944 B2 | 4/2012 | Boyer et al. |
| 8,332,238 B1 | 12/2012 | Allen |
| 8,489,415 B1 | 7/2013 | Ringold |
| 2003/0229516 A1 | 12/2003 | Nickerson |

(Continued)

OTHER PUBLICATIONS

Cutler et al., "The Potential for Cost Savings through Bundled Episode Payments", N Engl J Med. Mar. 22, 2012; 366(12): 1075-1077. doi:10.1056/NEJMp1113361. (Year: 2012).*

*Primary Examiner* — Aryan E Weisenfeld
*Assistant Examiner* — Joshua B Blanchette
(74) *Attorney, Agent, or Firm* — Christopher Pilling; Johan Eide; My Patent Guys

(57) ABSTRACT

Computer implemented methods and systems for bundled payment adjudication are disclosed. The method includes receiving patient information of patient. The patient information comprises at least patient identifier and clinical episode of patient. The method includes generating episode card for patient to avail healthcare services from one or more healthcare service providers for predefined time. The episode card includes claims submission information for healthcare services availed by patient from one or more healthcare service providers. The method includes receiving one or more claims associated with patient from at least one healthcare service provider. Each claim is associated with one or more healthcare services availed by patient for clinical episode using episode card. The method includes processing one or more claims for determining validity of each claim based on set of episode definition parameters. The method includes upon processing the claims, facilitating payment amount for one or more claims based on validity.

16 Claims, 17 Drawing Sheets

(56) References Cited

U.S. PATENT DOCUMENTS

| | | | |
|---|---|---|---|
| 2004/0103062 A1* | 5/2004 | Wood | G06Q 20/28 |
| | | | 705/41 |
| 2012/0215563 A1* | 8/2012 | Lassen | G06Q 50/22 |
| | | | 705/3 |
| 2014/0244275 A1 | 8/2014 | Parthasarathy | |
| 2014/0249864 A1* | 9/2014 | Sultan | G06Q 50/22 |
| | | | 705/4 |
| 2015/0127370 A1* | 5/2015 | Cornelis | G06Q 10/10 |
| | | | 705/2 |
| 2015/0199482 A1* | 7/2015 | Corbin | G06F 19/328 |
| | | | 705/2 |
| 2015/0294338 A1* | 10/2015 | Ketchel, III | G06Q 20/10 |
| | | | 705/2 |

\* cited by examiner

FIG. 5A

| PATIENT NAME | MEMBER ID | EPISODE NAME | ELIGIBLE? | PA REQUIRED | INITIATED | ACTION |
|---|---|---|---|---|---|---|
| XX-XXXX, YY-YYYY | 0560900145 | KNEE REPLACEMENT | N/A | NO | NO | DETAILS |
| JOHN, M | W000000000 | KNEE REPLACEMENT: (TEST PLAN) | YES | YES | YES | DETAILS CARD |
| KKK, RRR | 564 | ALL KNEE PROCEDURE | N/A | NO | NO | DETAILS |
| DDD, JJJ | W000000001 | KNEE REPLACEMENT | N/A | NO | NO | DETAILS |
| DDD, JJJ | W000000000 | KNEE REPLACEMENT: (TEST PLAN) | YES | YES | YES | DETAILS CARD |

PORTAL

DASHBOARD
PATIENTS

XYZ, ABC

YOU ARE HERE: PATIENTS > ELIGIBILITY DETAILS

| | |
|---|---|
| PATIENT NAME: JOHN, M | BIRTH DATE: JAN-25-1970 |
| EPISODE NAME: KNEE REPLACEMENT | INITIATED: YES |
| PHYSICIAN NAME: BLACKWELL, ELIZEBETH | INITIATOR NAME: BLACKWELL, ELIZEBETH |
| PA REQUIRED: YES | COINSURANCE: $0 |
| PAYOR TYPE: HEALTH PLAN | COPAY: $20 |
| DEDUCTIBLE: $2983.57 | PATIENT RESPONSIBILITY: $2983.57 |
| MAJOR PROCEDURE DATE: MAR-15-2018 | CHECKED DATE: MAR-11-2018 |

COMPUTER IMPLEMENTED METHODS AND SYSTEMS FOR BUNDLED PAYMENT ADJUDICATION

TECHNICAL FIELD

Embodiments of the disclosure relate generally to healthcare claims adjudication and, more particularly to, computer implemented methods and systems for bundled payment adjudication for healthcare services.

BACKGROUND

Traditionally, healthcare claims adjudication systems provision for separate payments to each healthcare service provider for the individual services they provide to a patient for an illness or during the course of treatment. This approach can result in fragmented care with minimal coordination across healthcare service providers and healthcare settings. In such cases, payment is based on a number of services offered by the healthcare service providers rather than the quality of care provided to patients.

Conventionally, in a bundled payment approach, all services related to an episode of care by healthcare providers (e.g., physician, surgeons, post-acute care providers) are reimbursed via a single payment. An entity financially at-risk for managing the bundled payment, herein referred to as the episode underwriter, receives a fixed, lump-sum payment from a payor, such as a health plan or employer group. The episode underwriter then pays for healthcare services consumed by the patient per the episode underwriter's contracted payment rates with the various healthcare providers. Similar to a health plan, the episode underwriter receives as underwriting margin the difference between the bundled payment and the payments made to the healthcare providers. The episode underwriter may be an insurance service provider or may be a healthcare provider, such as a physician group or hospital that desires to take financial risk to manage the episodes.

Traditionally, healthcare claims adjudication systems used by the healthcare providers have been designed to manage the entire healthcare claims of a member and are not well suited to manage bundled payments. Different techniques such as claims accumulators or dummy National Provider Identifier (NPI) numbers have been used to track expenses related to a particular clinical episode. However, such approaches have limitations, such as capturing the relevant claims as defined by the inclusion criteria parameters of a particular clinical episode, including but not limited to the relevant diagnoses, relevant procedures, relevant diagnostic related groups (DRGs), length of episode, and the network of providers. Additionally, determining the eligibility of the patient for bundled payment and determining patient responsibility have proven difficult with traditional healthcare claims adjudication systems. Moreover, the current healthcare claims adjudication systems are person dependent and require training and compliance with alternate adjudication methods, and are highly fallible and require significant reconciliation process after the episode.

In view of the above, there is a need for an automated bundled payment adjudication system that obviates the disadvantages of the existing healthcare claims adjudication systems, along with providing other benefits.

SUMMARY

Various embodiments of the present disclosure provide methods and systems for bundled payment adjudication for healthcare services.

In an embodiment, a computer implemented method is disclosed. The method includes receiving, by a processor, patient information of a patient. The patient information comprises at least a patient identifier and a clinical episode associated with the patient. The method includes generating, by the processor, an episode card for the patient to avail health care services from one or more healthcare service providers for a predefined time. The episode card comprises claims submission information for the healthcare services availed by the patient from the one or more healthcare service providers. The method includes receiving, by the processor, one or more claims associated with the patient from at least one health care service provider of the one or more health care service providers. Each claim is associated with one or more health care services availed by the patient in the predefined time for the clinical episode using the episode card. The method includes processing, by the processor, the one or more claims for determining validity of each claim of the one or more claims based on a set of episode definition parameters. The set of episode definition parameters are predefined for the clinical episode. The method further includes upon processing the one or more claims, facilitating, by the processor, a payment amount for the one or more claims of the at least one health care service provider based on the validity.

In another embodiment, a server system is disclosed. The server system comprises a memory to store instructions and a processor to execute the stored instructions in the memory and thereby cause the server system to receive patient information of a patient. The patient information comprises at least a patient identifier and a clinical episode associated with the patient. The server system is further caused to generate an episode card for the patient to avail health care services from one or more healthcare service providers for a predefined time. The episode card comprises claims submission information for healthcare services availed by the patient from the one or more healthcare service providers. The server system is caused to receive one or more claims associated with the patient from at least one health care service provider of the one or more health care service providers. Each claim is associated with one or more health care services availed by the patient in the predefined time for the clinical episode using the episode card. The server system is further caused to process the one or more claims for determining the validity of each claim of the one or more claims based on a set of episode definition parameters. The set of episode definition parameters are predefined for the clinical episode. The server system is furthermore caused to facilitate a payment for the one or more claims of the at least one health care service provider based on the validity upon processing of the one or more claims.

In yet another embodiment, a method is disclosed. The method includes receiving, by a processor, patient information of a patient. The patient information includes at least a patient identifier, a clinical episode associated with the patient, and a primary health insurance information associated with the patient. The method includes accessing, by the processor, eligibility information of the patient based on an eligibility file provided by an insurance service provider or an employer group. The eligibility file includes health insurance details of the patient. The method includes determining, by the processor, an eligibility of the patient for a bundled payment of claims for the clinical episode based on the eligibility information. The method includes upon determining the patient as an eligible candidate for the bundled payment of claims, generating, by the processor, an episode card for the patient to avail healthcare services from one or more healthcare service providers for a predefined time. The one or more healthcare service providers raise one or more claims for at least one health care service availed by the patient using the episode card. The method further includes processing, by the processor, the one or more claims for determining validity of each claim of the one or more claims based on a set of episode definition parameters. The set of episode definition parameters are predefined for the clinical episode. The method furthermore includes upon processing the one or more claims, facilitating, by the processor, a payment amount for the one or more claims of the at least one health care service provider based on the validity.

BRIEF DESCRIPTION OF THE FIGURES

For a more complete understanding of example embodiments of the present technology, reference is now made to the following descriptions taken in connection with the accompanying drawings in which:

FIG. 5A is an example representation of an interface displaying previous list of patient eligibility checks performed on the episode management platform, in accordance with an example embodiment;

FIG. 5B is an example representation of an interface displaying eligibility details of the patient on the episode management platform, in accordance with an example embodiment;

Figure 1:
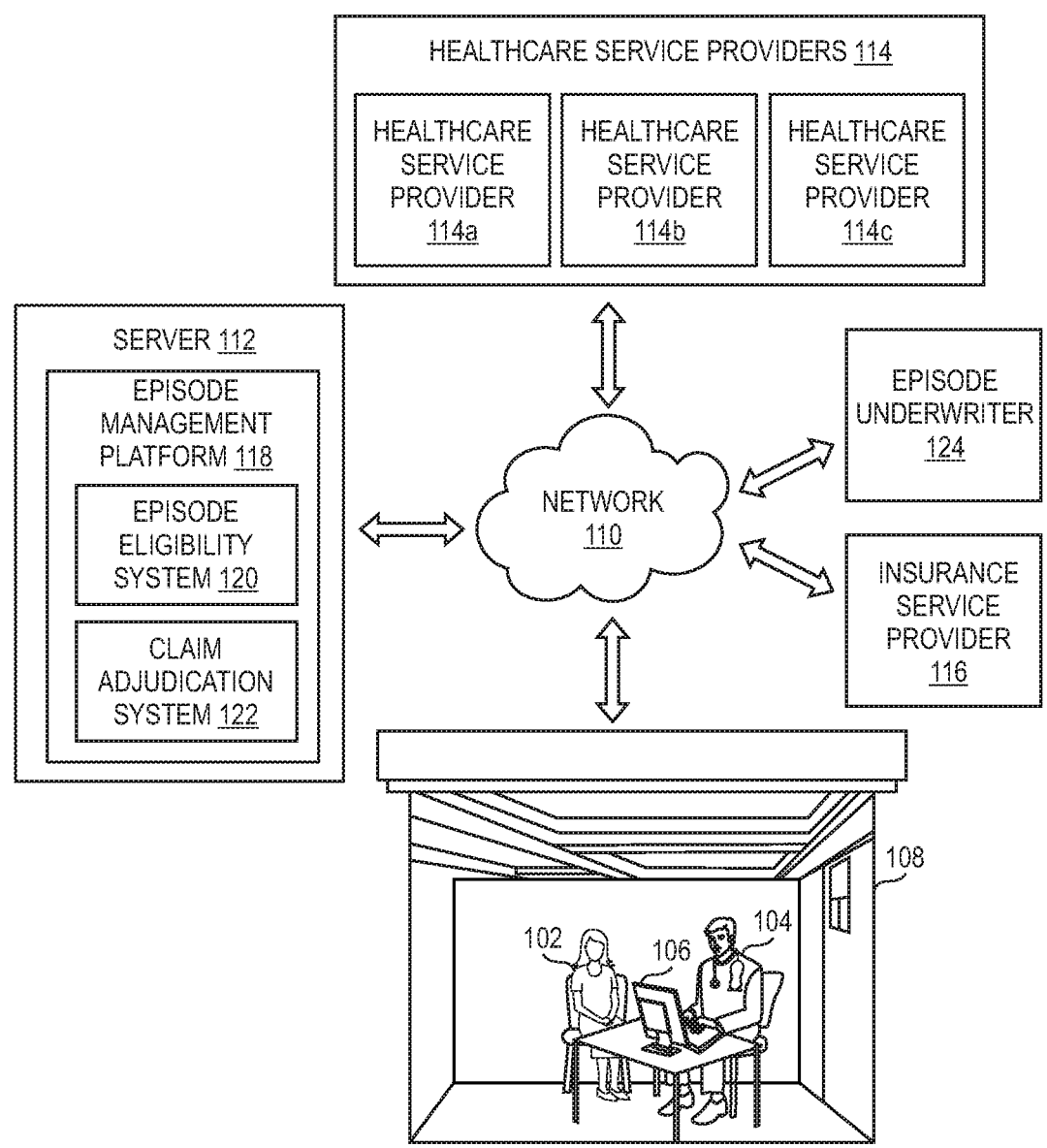
FIG. 1 is an illustration of an environment, where at least some example embodiments can be practiced.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. In other instances, systems and methods are shown in block diagram form only in order to avoid obscuring the present disclosure.

Reference in this specification to "one embodiment" or "an embodiment" means that a particular feature, structure, or characteristic described in connection with the embodiment is included in at least one embodiment of the present disclosure. The appearance of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

Overview

Various example embodiments of the present disclosure provide computer implemented methods and systems for bundled payment adjudication related to payments for availing healthcare services.

When a patient visits a healthcare professional with an illness or complications, his health condition is generally diagnosed to carry out the treatment procedures, and accordingly payment plan, schedule, and mode of payment are decided. For instance, if the health condition of the patient requires surgery, extended hospitalization, and post-operative care, the physician may recommend the patient to opt for bundled payment. The bundled payment adjudication of healthcare claims is managed by an episode management platform. The episode management platform comprises an episode eligibility system and a claim adjudication system. The episode eligibility system determines eligibility of the patient for bundled payment and the claim adjudication system resolves the claims raised by healthcare service providers. The healthcare professional (e.g., a physician) creates a clinical episode corresponding to the health condition of the patient and checks eligibility of the patient for the bundled payment via the episode eligibility system. The episode eligibility system stores the bundled payment eligibility of members (via eligibility data file feeds from payors) and also retrieves insurance details of the patient from an insurance service provider based on a primary health insurance information. The eligibility files are used by the episode eligibility system to determine the patient's eligibility for bundled payment relating to a particular clinical episode.

The patient is added to the claim adjudication system if the patient is found to be eligible for the bundled payment. The episode eligibility system determines a patient responsibility for expenses of the clinical episode and the bundled payment. The patient responsibility may be a contracted payment rate for example, a sum of deductible amount, coinsurance amount and a copay amount as stipulated by the insurance service provider of the health plan that has to be paid by the patient for availing bundled payment towards the clinical episode. Additionally, the episode eligibility system generates an episode card that can be used by the patient to avail healthcare service from multiple healthcare service providers providing healthcare services for the patient opting for bundled payment of claims. The episode card comprises claim submission information that allow for proper adjudication of claims, specifically the patient's name, member ID, group ID and plan ID pursuant to the particular clinical episode. The healthcare service providers submit claims for the healthcare services availed by the patient using the episode card to the claim adjudication system in the episode management platform. The claim adjudication system within the episode management platform determines the validity of the claims for the clinical episode. The claim adjudication system releases the payments to the healthcare service providers if the submitted claims are found to be valid claim for that clinical episode.

The term 'bundled payment' as used herein refers to a bundled payment approach, wherein all services related to an episode of care, including physician services and post-acute care providers are paid to an episode underwriter via a single payment from the insurance service provider. It shall also be noted that the terms 'user device' and 'device' are used interchangeably throughout the present description.

FIG. 1 shows an example representation of an environment 100 related to at least some example embodiments of the present disclosure. An example representation of the environment 100 is shown depicting a wireless communication network (e.g., a network 110) that connects entities such as, a healthcare facility 108, healthcare service providers 114, an insurance service provider 116, an episode underwriter 124 and a server 112. The healthcare service providers 114a, 114b, 114c (hereinafter collectively referred to as the healthcare service providers 114) may include hospitals, physiotherapy centers, diagnostic centers, rehabilitation centers, post-operative care providers that may be used by the patient 102 for a particular clinical episode of care. It shall be noted that the healthcare service providers 114 are shown for the sake of simplicity and example purposes only and the patient 102 may avail healthcare services from a plurality of healthcare providers during a course of the treatment of the patient 102.

The server 112 comprises an episode management platform 118 that is configured to manage bundled payment of claims for patients who avail healthcare services from the healthcare service providers 114. It shall be noted that the healthcare facility 108 is also a healthcare provider and has been depicted as a separate entity for example purposes. The episode management platform 118 includes an episode eligibility system 120 and a claim adjudication system 122. The episode eligibility system 120 performs eligibility check of the patient for bundled payment relating to a clinical episode and the claim adjudication system 122 settles claims to healthcare services providers for health care services availed by patients.

As seen from FIG. 1, a patient 102 presents to a physician 104 with a health condition that may require a major procedure at the healthcare facility 108 and/or need to avail healthcare services for the patient 102 from the healthcare service providers 114. The physician 104 recommends the patient to opt for a bundled payment to avail healthcare services from one or more healthcare providers (e.g., the healthcare service providers 114) based on the diagnosis of the health condition. However, eligibility of the patient 102 for the bundled payment has to be determined based on a health insurance plan availed by the patient from the insurance service provider 116 and/or a predetermined contractual arrangement between an insurance service provider 116 and the episode underwriter 124. The episode underwriter 124 is an entity that provides the episode definition parameters such as, procedures, valid diagnoses, valid health care provider network, episode lengths and episode start for a clinical episode. The episode definition parameters are stored in the server 112. The physician 104 through one or more devices, for example, a device 106 checks patient eligibility for the bundled payment relating to a clinical episode. The term 'clinical episode' as used herein refers to a health condition diagnosed by the physician 104 that may require healthcare services for the patient 102. The device 106 may be any communication device having hardware components for enabling a UI of the episode eligibility system 120 to be presented on the device 106. The device 106 may be capable of being connected to a wireless communication network (such as network 110). Examples of the device 106 include a mobile phone, a smart telephone, a computer, a laptop, a PDA (Personal Digital Assistant), a Mobile Internet Device (MID), a tablet computer, an Ultra-Mobile personal computer (UMPC), a phablet computer, a handheld personal computer and the like.

The device 106 can communicate with the server 112 to access the episode eligibility system 120 through the communication network 110. The communication network 110 represents any distributed communication network (wired, wireless or otherwise) for data transmission and receipt among two or more points. The communication network 110 may as an example, include standard and/or cellular telephone lines, LAN or WAN links, broadband connections (ISDN, Frame Relay, ATM), wireless links, and so on. Preferably, the communication network 110 can carry TCP/IP protocol communications, and HTTP/HTTPS requests made by the user devices and the server system can be communicated over such communication networks 110. A preferred example of the communication network 110 is the Internet, which may be a combination of various communication technologies.

The episode management platform 118 manages bundled payment adjudication for the clinical episode associated with the patient 102. The episode eligibility system 120 provides a physician interface that displays one or more User Interfaces (UIs) for determining the patient eligibility. For example, the physician interface is accessed by the physician 104 via the device 106 to provide patient information associated with the patient 102 for checking the patient's eligibility for the bundled payment. The patient information includes a patient identifier (ID), a clinical episode associated with the patient, and a primary health insurance information associated with the patient. The episode eligibility system 120 determines the patient eligibility for the clinical episode based on stored eligibility of members that uses eligibility file provided by payors (e.g., the insurance service provider 116). The eligibility file includes health insurance details of the patient 102. The eligibility files may take the form of EDI 834 files, CSV files or some other type of automated feed or API. The server 112 may contact the insurance service provider 116 through the communication network 110 for acquiring eligibility file associated with the patient 102. If the patient 102 is found eligible for the bundled payment, the episode eligibility system 120 at the server 112 may calculate the patient responsibility and a total bundled claim for the particular clinical episode of care and may generate an episode card for the patient 102. The patient eligibility, the patient responsibility and the episode card may be shared with the physician 104 on the physician interface of the device 106. The physician 104 may generate a clinical episode for the patient 102 in the episode management platform 118 and may download the episode card provided by the server 112. The physician 104 provides the episode card to the patient 102. The episode card can be used by the patient 102 to avail health care services from the healthcare service providers 114 for a predefined time.

In an embodiment, the episode eligibility system 120 adds the name of the patient 102, member ID and an eligibility period (also referred to as 'a predefined time') corresponding to a length of the clinical episode to the claim adjudication system 122 for enabling claim settlement during the clinical episode. The episode eligibility system 120 and the claim adjudication system 122 may be applications resting at the server 112 in form of a web application or a mobile application. The mobile application may be available for download on Google® Playstore, Apple® app store, etc. The instances of the application can be made available at the user devices, such as the user device 106.

In an embodiment, the episode card is valid for a list of healthcare service providers. The patient 102 can choose any healthcare service provider, such as a healthcare service provider 114a, 114c from the healthcare service providers 114 for availing the healthcare service by using the episode card. However, it shall be noted that healthcare services can be availed by the patient 102 from the healthcare service provider 114 showing the episode card for the predefined time based on the eligibility period indicating validity of the episode card.

In an embodiment, the healthcare service providers 114 (e.g., 114a, 114c) submit the claims to the claim adjudication system 122 for the healthcare services availed by the patient 102 during the eligibility period. The claim adjudication system 122 determines the validity of the claims submitted by the healthcare service providers (e.g., healthcare service providers 114a, 114c) by classifying the claims as a valid claim or an invalid claim based on the episode definition parameters stored in the server 112. If the claims are found to be valid claims, the server 112 may contact the episode underwriter 124 for settling payment for the claims submitted by the healthcare service providers 114. The episode underwriter 124 may issue the payment to the healthcare service providers 114 via the episode management platform 118. In an embodiment, the server 112 can be a cloud based server. Alternatively or additionally, the server 112 may be located at a centralized location. The server 112 hosts and manages the episode eligibility system 120 and the claim adjudication system 122 of the episode management platform 118, and provides instances of the episode eligibility system 120 and the claim adjudication system 122 to other entities such as the healthcare facility 108, healthcare service providers 114 and the insurance service provider 116.

Figure 10:
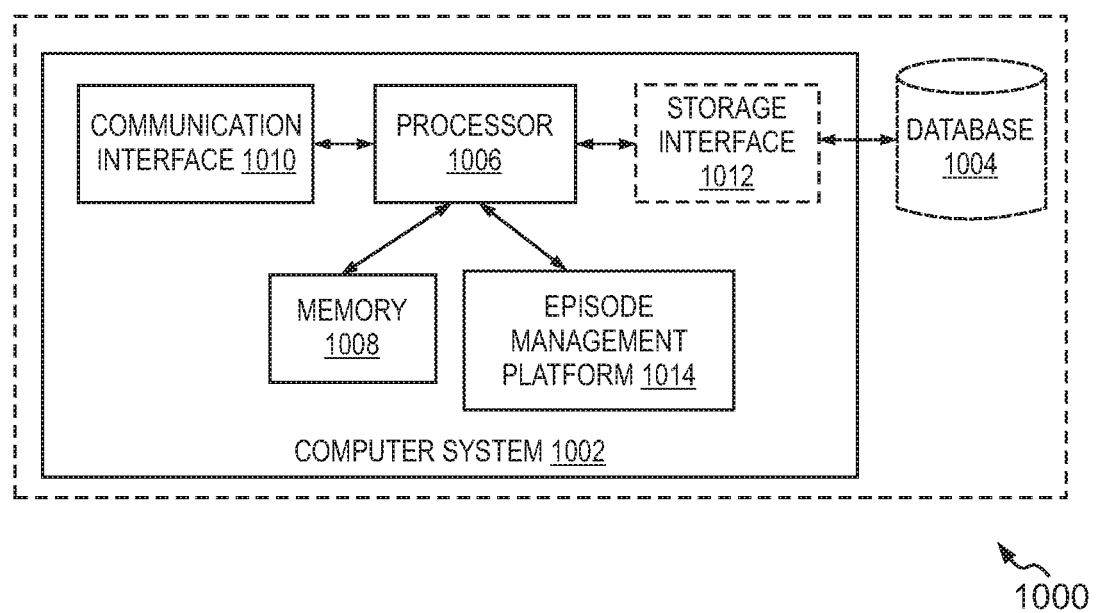
FIG. 10 is a block diagram of a server of FIG. 1, in accordance with an example embodiment.

It is noted that the instructions (or the executable code) configuring the episode management platform 118 are stored in a memory of the server 112, and the instructions are executed by a processor (for example, a single-core or a multi-core processor) included within the server 112, as is exemplarily shown with reference to FIG. 10. However, once the episode management platform 118 is installed on the device 106, via its processor, the episode management platform 118 can control the entire process of bundled payment adjudication.

Various embodiments of the present description are explained with reference to FIGS. 2A-2B to 10.

Figure 2A:
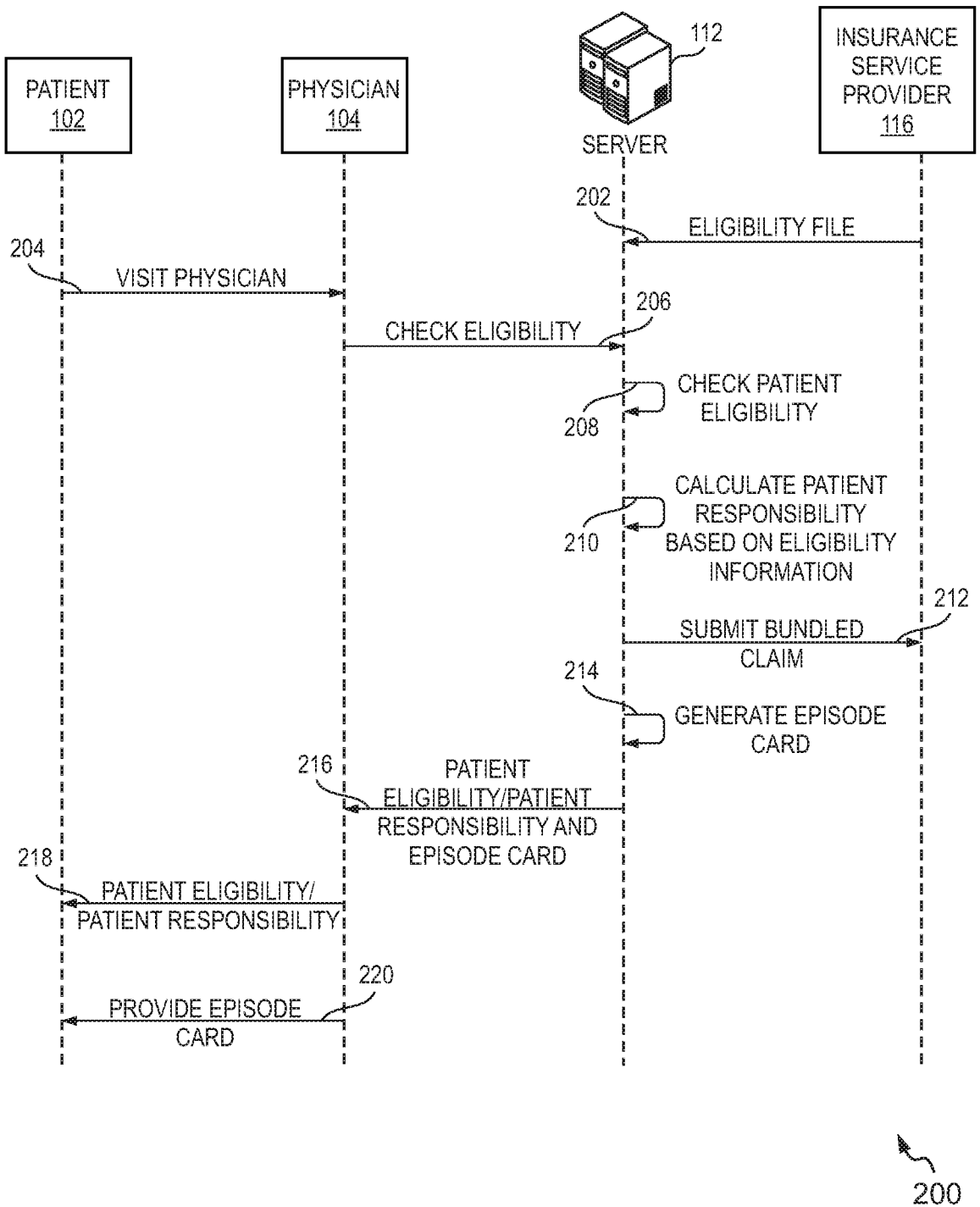
FIG. 2A is a sequence flow diagram of bundled payment adjudication for checking eligibility of a patient, in accordance with an example embodiment.

FIG. 2A is a sequence diagram 200 of bundled payment adjudication for checking eligibility of a patient, in accordance with an example embodiment. The sequence of operations of the method need not to be necessarily executed in the same order as they are presented. Further, one or more operations may be grouped together and performed in form of a single step, or one operation may have several sub-steps that may be performed in parallel or in sequential manner.

At operation 202, the insurance service provider 116 provides the eligibility file of the patient 102 to the server 112. An example of the format of the eligibility files can be EDI 834 files, CSV files, or some other type of automated feed or API. The eligibility file provides health insurance details of the patient eligible for bundled payments and is stored in a database associated with the server 112.

At operation 204, the patient 102 visits the healthcare facility 108 to consult with the physician 104 for health issue he/she is facing. The physician 104 diagnoses health condition of the patient 102. If the health condition of the patient requires extended care from one or more healthcare service providers, the physician may suggest the patient 102 to opt for bundled payment for a clinical episode. The physician 104 may request the patient 102 to furnish a primary insurance card that includes primary health insurance information. The primary insurance card may be used by the physician 104 to check for patient eligibility for the bundled payment.

At operation 206, the physician 104 checks eligibility of the patient 102 for bundled payment of claims for the clinical episode. For instance, the physician 104 may access an application of an episode management platform (e.g., the episode management platform 118) on the device 106 for determining the patient eligibility. In an example, the physician 104 provides patient information of the patient 102 such as patient identifier, patient name, clinical episode associated with the patient 102 and the primary health insurance information associated with the patient 102 on a corresponding UI of the episode management platform 118. Providing patient and insurance details is further explained with reference to FIGS. 4A-4D.

At operation 208, the server 112 determines whether the patient 102 is eligible for bundled payment for the clinical episode. The patient eligibility on a particular clinical episode is determined by the server 112 based on the eligibility file provided by the insurance service provider 116 (see, operation 202) and other episode information contained within the episode eligibility system 120, such as the clinical episodes covered by the insurance service provider 116 and/or episode definition parameters defined by the episode underwriter 124.

At operation 210, if the patient 102 is found to be eligible for bundled payment corresponding to the clinical episode, the patient responsibility for the clinical episode is calculated using eligibility information of the patient 102 retrieved from the eligibility files provided by the insurance service provider 116 or an employer group. Patient responsibility refers to an amount payable by the patient 102 for availing bundled payment towards the healthcare services availed from healthcare service providers (e.g., the healthcare service providers 114) by the patient 102 during the course of treatment for the clinical episode.

At operation 212, the server 112 submits a total bundled claim on behalf of the patient 102 to the insurance service provider 116. The total bundled claim is determined by the server 112 based on the clinical episode of the patient 102 and submitted to the insurance service provider 116 after verifying the patient eligibility for bundled payment of the clinical episode. In an embodiment, the total bundled claim is either submitted to the health plan or queued for invoicing process of an employer. In an embodiment, the server 112 may also allow customized adjudication of claims, depending upon requirements of the insurance service provider 116.

At operation 214, an episode card is generated for the patient 102 by the episode management platform 118 at the server 112. For instance, when the total bundled claim is submitted to the insurance service provider 116 for the clinical episode, an episode card is generated for the patient 102 by the server 112. In an example, the episode card may be generated in a Portable Document Format (PDF). Alternatively, the episode card can be generated in any other document formats, such as MS-Word or any similar format. The episode card may allow the patient 102 to avail health care services from the healthcare service providers 114 for a predefined time. The episode card includes claim submission information for the healthcare services availed by the patient from the one or more healthcare service providers. The claim submission information helps in proper adjudication of claims through the claim adjudication system 122. In an embodiment, the episode card includes patient information (patient name, member ID, group ID and plan ID), clinical episode for which the episode card is valid, the claim submission information and one or more terms and conditions for the bundled payment of claims.

At operation 216, the patient eligibility, patient responsibility and the episode card are made available to the physician 104 on the device 106 via the UI of the episode management platform 118. At operation 218, the physician 104 provides information related to the patient eligibility and the patient responsibility to the patient 102. The physician 104 may also explain the benefits of the bundled payment to the patient 102.

At operation 220, the physician 104 provides the episode card to the patient 102. In an embodiment, the episode card can be used by the patient 102 to avail healthcare service at a healthcare service provider pursuant to the episode card's list of healthcare providers for availing healthcare services such as surgical procedures, diagnoses or therapy as required by the patient 102. For example, if the patient 102 is associated with a clinical episode of renal failure, the bundled claim involves cost of procedures such as kidney transplant, dialysis and post-operative therapy that can be availed from different healthcare service providers pursuant to the episode card's valid procedures for the predefined time (eligibility period) as stipulated by the episode management platform 118. An example of the episode card is shown and explained with reference to FIG. 5C.

Figure 2B:
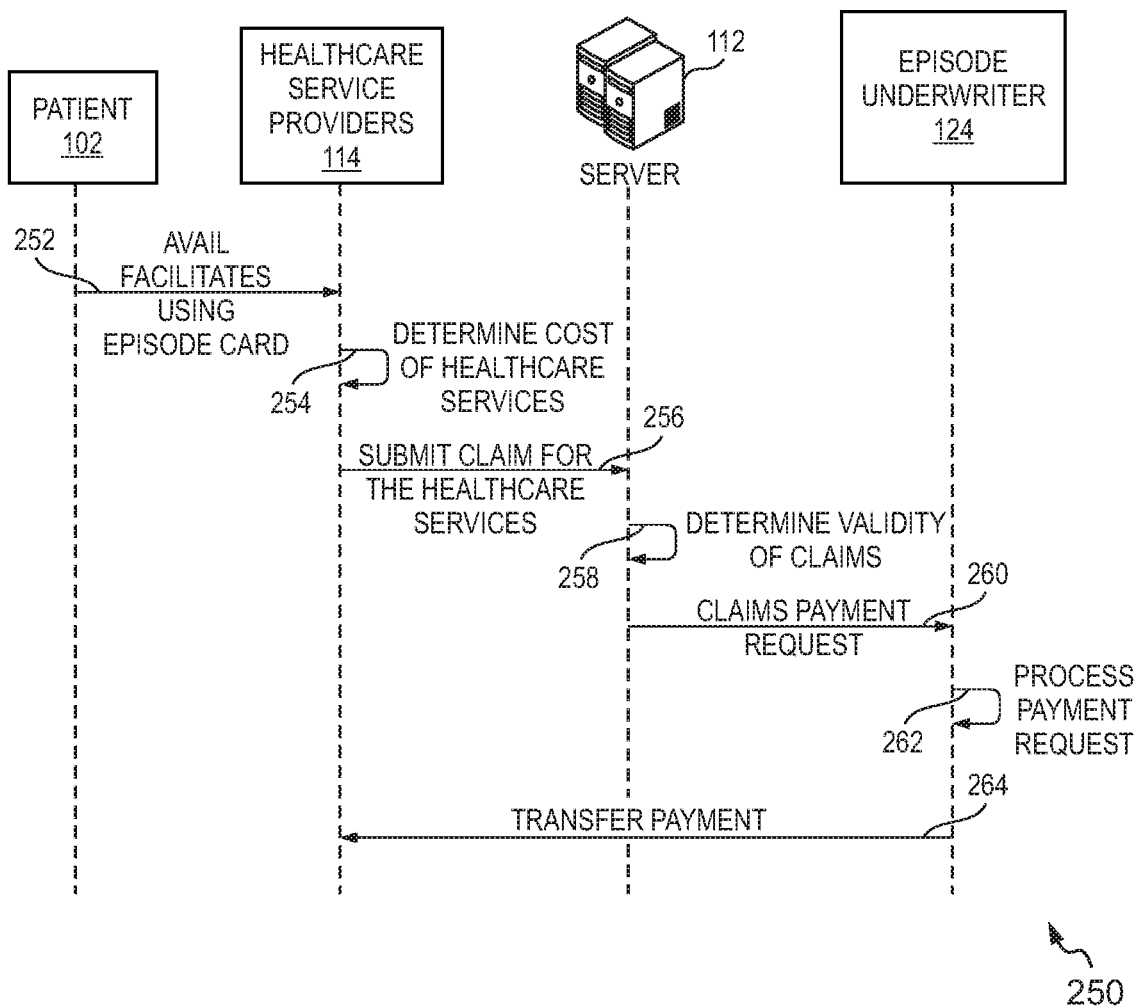
FIG. 2B is a sequence flow diagram of bundled payment adjudication for settling claims, in accordance with an example embodiment.

FIG. 2B is a sequence diagram 250 of bundled payment adjudication for settling claims, in accordance with an example embodiment. The sequence of operations as shown in the sequence diagram 250 need not to be necessarily executed in the same order as they are presented. Further, one or more operations may be grouped together and performed in form of a single step, or one operation may have several sub-steps that may be performed in parallel or in sequential manner.

At operation 252, the patient 102 avails healthcare facilities at the healthcare service provider 114 using the episode card. In an example, the patient 102 may undergo a knee replacement surgery at a hospital facility X and physiotherapy sessions with a service provider Y using the episode card. It shall be noted that the hospital facility X and the service provider Y are healthcare service providers pursuant to the episode card's list of healthcare providers providing valid procedures that cover the clinical episode of knee replacement.

At operation 254, the healthcare service providers 114 calculate the cost of the healthcare services provided to the patient 102 for the clinical episode. For example, if the patient 102 was hospitalized for a specific clinical episode (e.g., accident) at a hospital facility (e.g., the healthcare facility 108), the hospital facility can determine total cost of hospitalization for the patient 102. It shall also be noted that the patient 102 may access facilities offered by different healthcare service providers or different hospital facilities pursuant to the episode card's list of healthcare providers and in such cases each of the healthcare service provider and/or the hospital facility estimate a cost for the healthcare service offered to the patient 102.

At operation 256, the healthcare service provider 114 submits the claims for the healthcare services to the server 112. In an embodiment, the claims are submitted by the healthcare service provider 114 to the claim adjudication system 122 for validating the claims. In cases where the patient 102 avails services from different hospital facilities and/or healthcare service providers, the claims of each hospital facilities and/or healthcare service providers are submitted to the claim adjudication system 122. In an embodiment, each of the claims submitted by the healthcare service providers 114 and/or hospital facilities are re-priced based upon the contracted payment rate between the healthcare service providers 114 and the episode underwriter 124.

At operation 258, the server 112 may determine the validity of the claims submitted by the healthcare service provider 114 by classifying each claim as a valid claim or an invalid claim based on the episode definition parameters stored in a database of the server 112. For instance, the claims raised by each of the healthcare service providers for each service availed by the patient 102 is compared against the episode definition parameters of the clinical episode as determined by the episode management platform 118 to determine healthcare services that are covered by the bundled payment for the clinical episode.

At operation 260, if the claims are found to be valid claims, the server 112 issues a claim payment request to the episode underwriter 124. For example, assuming the patient 102 presented with a clinical episode of cardiac discomfort and the patient 102 was hospitalized for cardiac problems, the patient eligibility is determined for the clinical episode of cardiac problem and corresponding treatments. However, the patient 102 also avails services of an ophthalmologist during his stay in the hospital for which he is not eligible and the clinical episode (e.g., an eye test) is not covered by the bundled claim submitted earlier by the physician 104. In such cases, the claim raised by the ophthalmology department may be turned down as the invalid claim for the bundled payment. However, services availed with respect to the clinical episode of cardiac discomfort are deemed as valid claims and the claim requests corresponding to the valid claims for the clinical episode are provided to the episode underwriter 124.

At operation 262, the episode underwriter 124 processes the claim payment request. The claim payment request comprises payment amount for the healthcare service availed by the patient 102. At operation 264, the episode underwriter 124 transfers the payment amount to the healthcare service providers 114.

Figure 3:
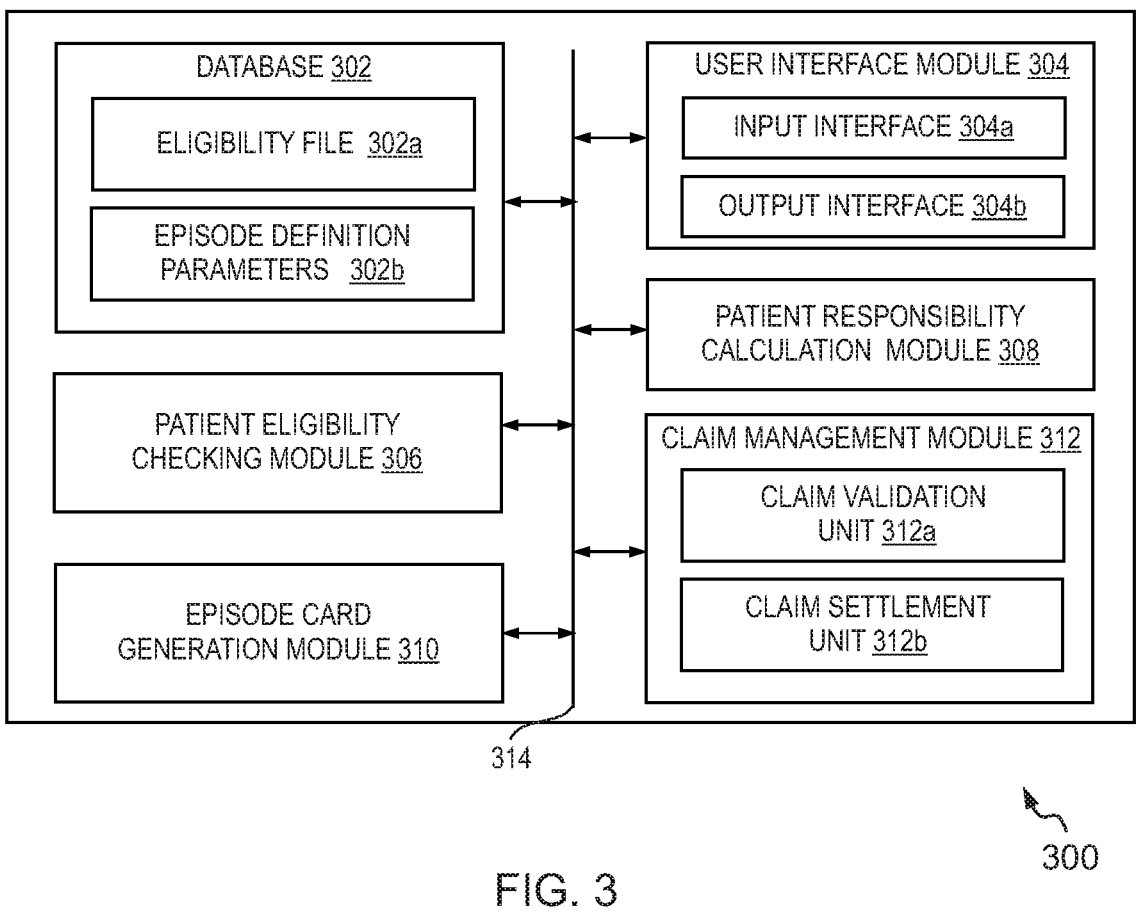
FIG. 3 is a functional block diagram of a system for bundled payment adjudication for healthcare services, in accordance with an example embodiment.

FIG. 3 is a block diagram of a system 300 for bundled payment adjudication of healthcare services, in accordance with an example embodiment. The system 300 may be embodied in a server system, for example, the server 112 or an electronic device, such as, the device 106 accessible by a healthcare service provider, such as the physician 104. The system 300 comprises a database 302, a user interface module 304, a patient eligibility checking module 306, a patient responsibility calculation module 308, an episode card generation module 310, a claim management module 312 and a centralized circuit system 314.

The database 302 is configured to store a plurality of eligibility files 302a associated with a plurality of patients. The eligibility files 302a are received from a plurality of insurance service providers providing insurance services to the plurality of patients and a plurality of employer groups providing health insurance services to their employees. The database 302 is also configured to store a set of episode definition parameters 302b for each clinical episode of a plurality of clinical episodes that indicate eligibility for bundled payment of claims as defined by an episode underwriter (e.g., the episode underwriter 124). The set of episode definition parameters 302b may include information such as procedures, valid diagnosis, valid provider network/health care service providers, episode lengths and episode start for a clinical episode.

The user interface (UI) module 304 is configured to present one or more UIs for facilitating bundled payment adjudication for healthcare services availed by the patient 102. The UI module 304 comprises an input interface 304a and an output interface 304b. The input interface 304a is configured to receive patient information associated with the patient 102. The patient information may include but are not limited to patient identifier, clinical episode associated with the patient, and primary health insurance information associated with the patient. The input interface 304a is also configured to receive one or more claims associated with the patient 102 from one or more health care service providers, such as the healthcare service providers 114. Examples of the input interface 304a may include, but are not limited to, a keyboard, a mouse, a joystick, a keypad, a touch screen, soft keys, and the like. The output interface 304b is configured to display a patient eligibility and a patient responsibility for a clinical episode of care. The output interface 304b is also configured to display an episode card that may be downloaded and printed for a user (e.g., the physician 104) of the system 300. Examples of the output interface 304b may include, but are not limited to, a display such as a light emitting diode display, a thin-film transistor (TFT) display, a liquid crystal display, an active-matrix organic light-emitting diode (AMOLED) display, and the like.

The patient eligibility checking module 306 is in communication with the database 302 and the UI module 304. The patient eligibility checking module 306 is configured to determine/check eligibility of the patient 102 for the bundled payment of claims for a specific clinical episode based on an eligibility file (associated with the patient 102) stored in the database 302.

The patient responsibility calculation module 308 is in communication with the patient eligibility checking module 306, the database 302 and the UI module 304. Upon determining that the patient 102 is eligible for the bundled payment of claims for the clinical episode, the patient responsibility calculation module 308 is configured to calculate a patient responsibility for the clinical episode based on a health plan scheme provided by the insurance service provider 116. If the health plan scheme is an employer group carve-out scheme, the patient responsibility calculation module 308 calculates the patient responsibility based on eligibility information received from the eligibility file stored in the database 302. If the health plan scheme is health plan payor scheme, the patient responsibility calculation module 308 calculates the patient responsibility based on financial information associated with the patient. The financial information is provided by the insurance service provider 116 of the patient 102 upon receiving a financial information request from the system 300. In an embodiment, the financial information includes a deductible amount, a copay amount, a coinsurance amount and an out of pocket (OOP) max amount.

The episode card generation module 310 is in communication with the patient eligibility checking module 306 and the UI module 304. The episode card generation module 310 is configured to generate an episode card for the patient if the patient is found eligible for the bundled payment. In an embodiment, the generated episode card may be provided to the UI module 304 for facilitating download of the episode card. The episode card may include a patient information, a list of healthcare service providers, a validity information of the episode card and one or more terms and conditions for the bundled payment of claims.

The claim management module 312 is in communication with the database 302 and the UI module 304. The claim management module 312 is configured to receive, manage and settle claims submitted by the healthcare service providers 114 for the healthcare services availed by the patient 102 in a predefined time for the clinical episode using the episode card. The claim management module 312 includes a claim validation unit 312a and a claim settlement unit 312b. The claim validation unit 312a is configured to determine the validity of the claims by classifying each claim as a valid claim or an invalid claim based on the set of episode definition parameters stored in the database 302 for the clinical episode associated with the patient 102. In case of an invalid claim, the claim validation unit 312a is further configured to generate a notification for the patient 102 and the health care service provider related to the invalid claim. The notification may include reasons for determining the invalid claim and an invalid claim payment amount to be paid by the patient 102 to the health care service provider associated with the invalid claim. The claim settlement unit 312b is in communication with the claim validation unit 312a. The claim settlement unit 312b is configured to settle claims that are found valid by the claim validation unit 312a to respective health care service providers from whom the patient had availed health care services for the clinical episode using the episode card.

In an embodiment, upon determining at least one valid claim, the claim settlement unit 312b is configured to facilitate payment of a payment amount (based on a contracted payment rate) for the health care service associated with the at least one valid claim to the healthcare service provider (e.g., the healthcare service provider 114a).

The database 302, the user interface module 304, the patient eligibility checking module 306, the patient responsibility calculation module 308, the episode card generation module 310, the claim management module 312 may be configured to communicate with each other via or through the centralized circuit system 314. The centralized circuit system 314 may be various devices configured to, among other things, provide or enable communication between the modules (302-312) of the system 300. In certain embodiments, the centralized circuit system 314 may be a central printed circuit board (PCB) such as a motherboard, a main board, a system board, or a logic board. The centralized circuit system 314 may also, or alternatively, include other printed circuit assemblies (PCAs) or communication channel media. In some embodiments, the centralized circuit system 314 may include appropriate storage interfaces to facilitate communication among the modules (302-312). Some examples of the storage interface may include, for example, an Advanced Technology Attachment (ATA) adapter, a Serial ATA (SATA) adapter, a Small Computer System Interface (SCSI) adapter, a RAID controller, a SAN adapter or a network adapter.

Figure 4A:
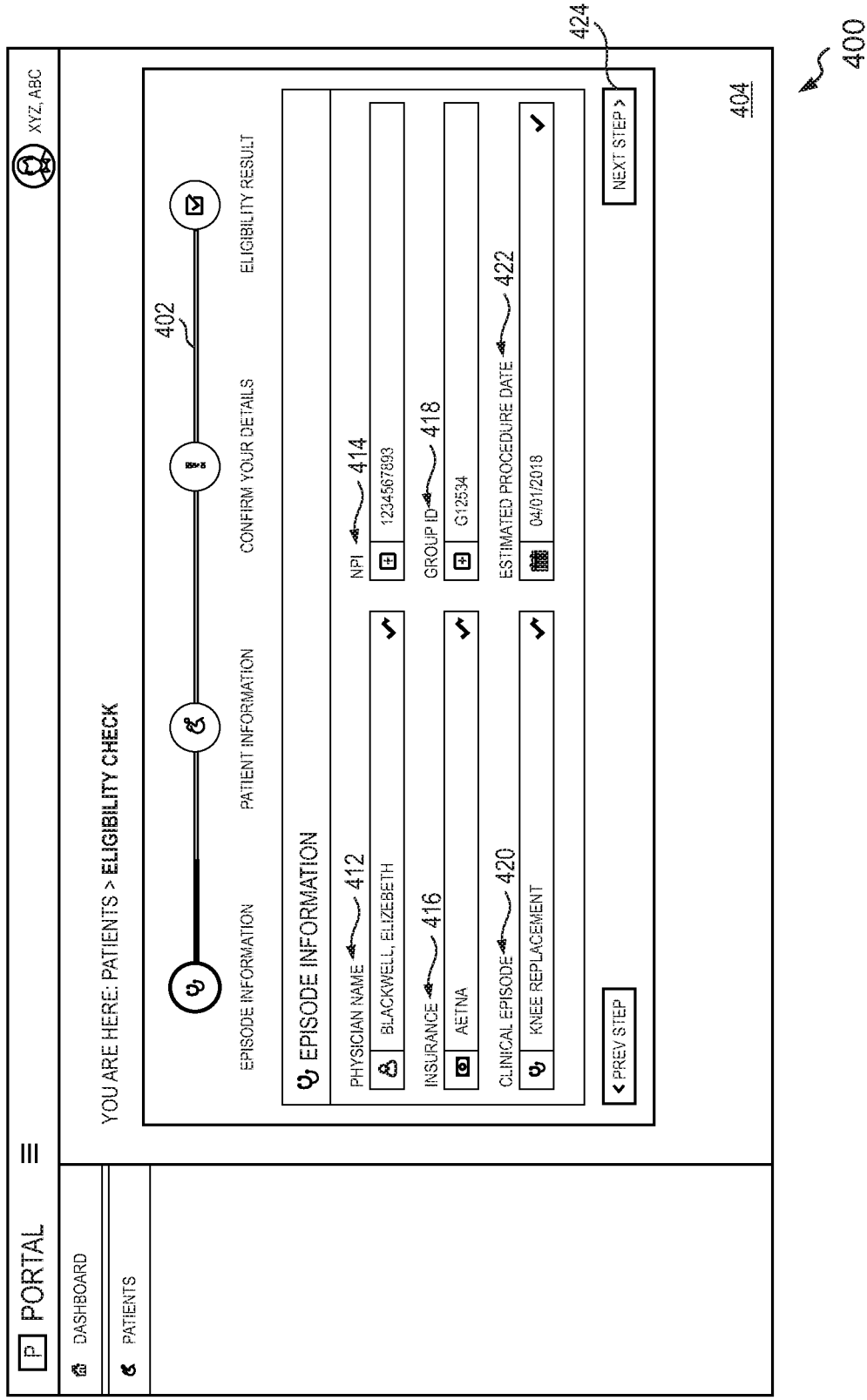
FIG. 4A is an example representation of an interface of an episode management platform depicting acquisition of clinical episode information from a patient for performing an eligibility check, in accordance with an example embodiment.
Figure 4B:
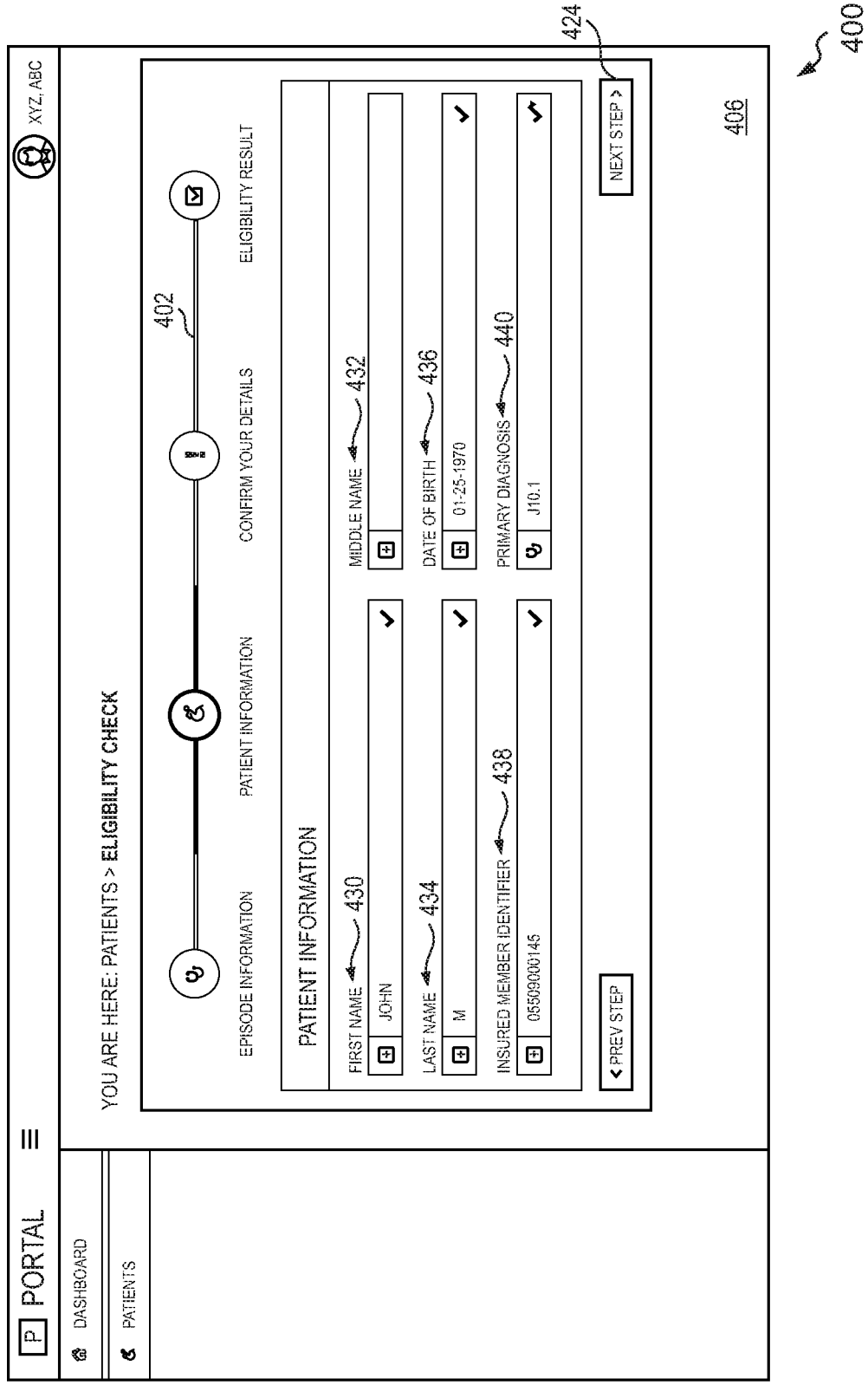
FIG. 4B is an example representation of an interface of the episode management platform depicting acquisition of patient details for performing an eligibility check, in accordance with an example embodiment.
Figure 4C:
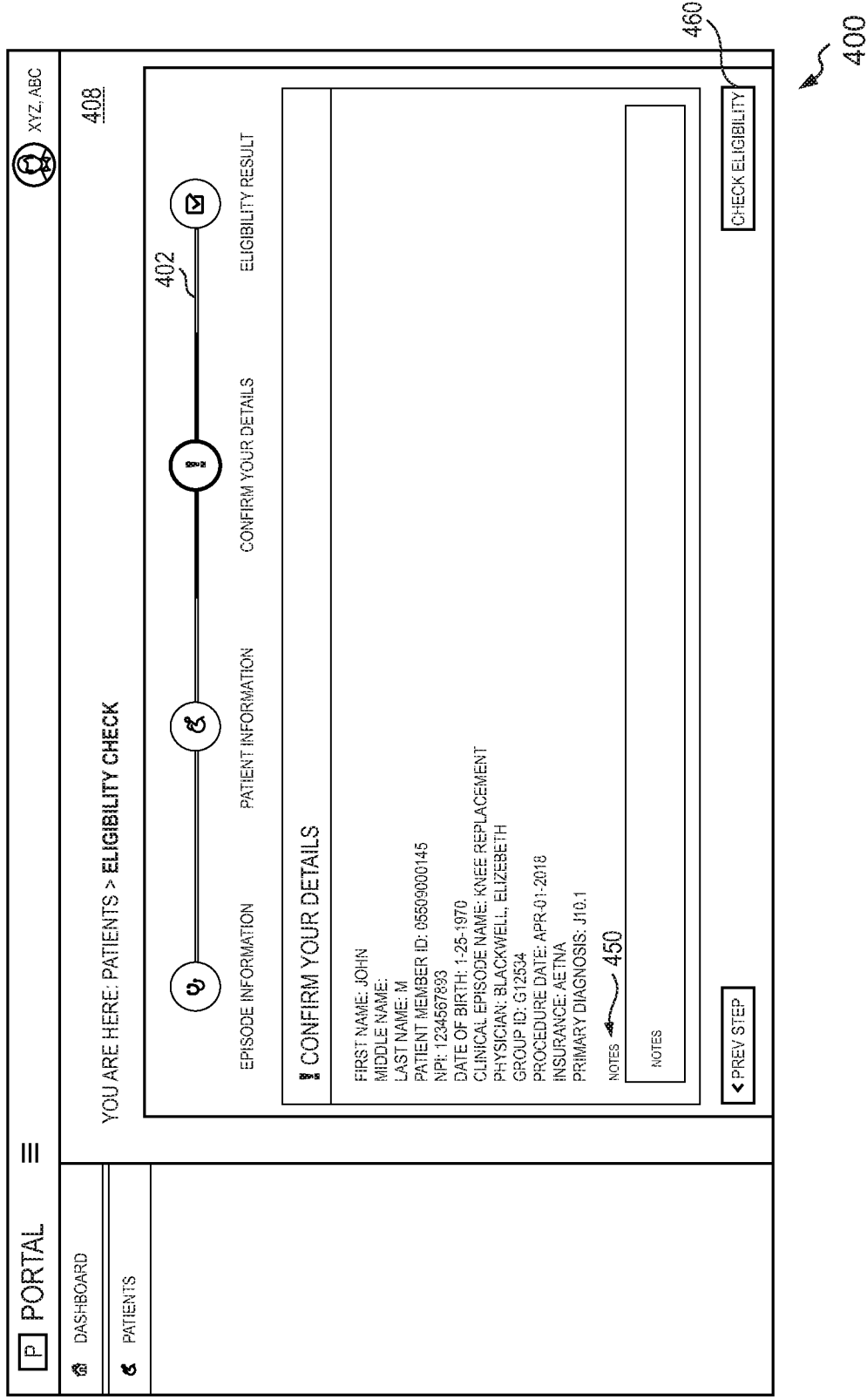
FIG. 4C is an example representation of an interface of the episode management platform displaying patient details acquired from the patient for performing the eligibility check, in accordance with an example embodiment.
Figure 4D:
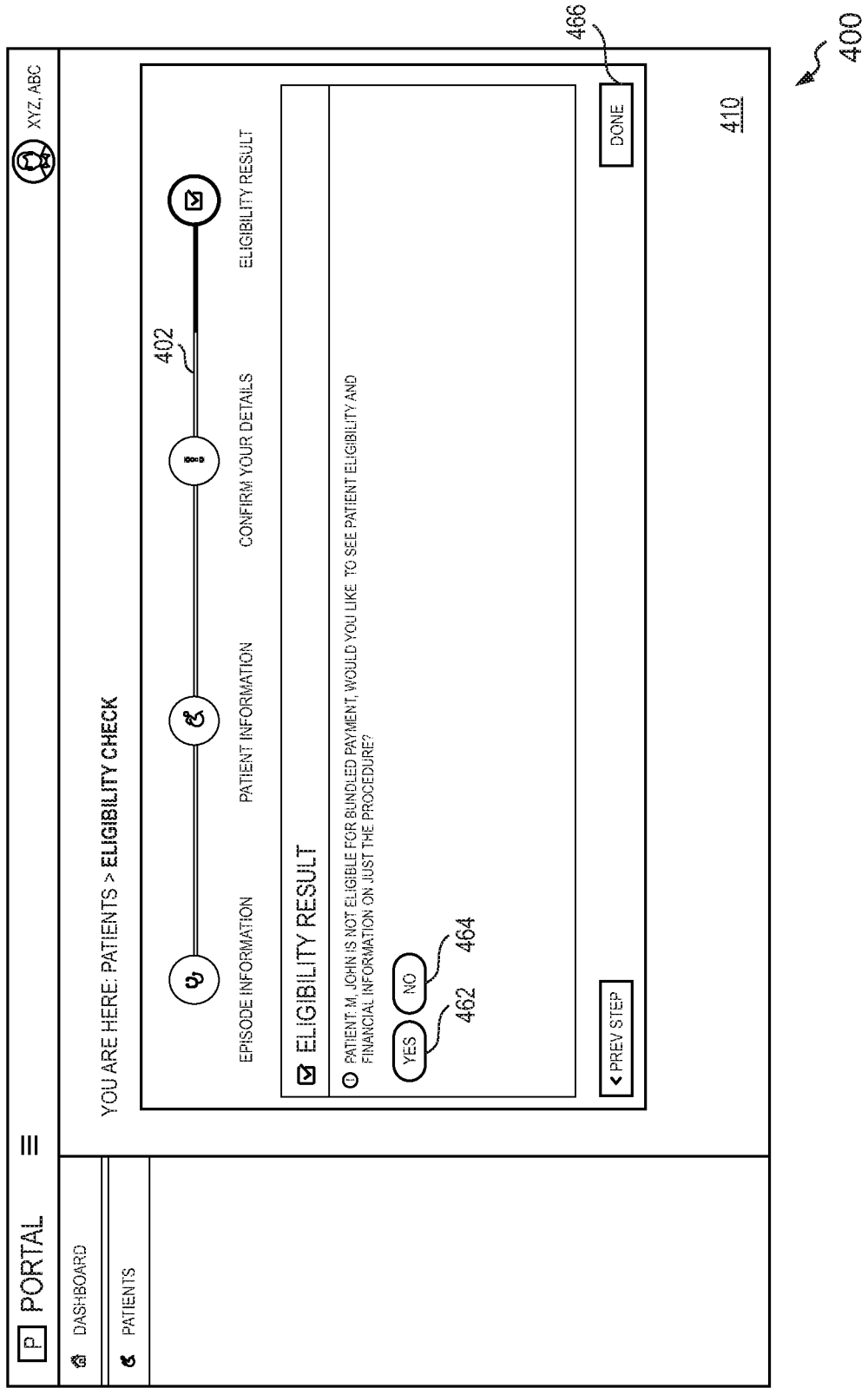
FIG. 4D is an example representation of an interface of the episode management platform displaying eligibility check result, in accordance with an example embodiment.

FIG. 4A is an example representation of an interface 400 of the episode management platform for collecting episode information and performing an eligibility check, in accordance with an example embodiment. It shall be noted that the interface 400 as described in FIG. 4A is accessible to a physician (such as the physician 104). Similarly, the pages 406, 408, 410 of the episode management platform 118 as described in the FIGS. 4B-4D are accessible by the physician (such as the physician 104) on the device 106.

The interface 400 includes a progress tracker 402 depicting progress in submitting documents/data essential for performing a patient eligibility test. The progress tracker 402 displays progress to a physician by highlighting icons such as, an episode information icon corresponding to an episode information page 404, a patient information icon corresponding to a patient information page 406 (see, FIG. 4B), confirmation icon corresponding to a confirmation page 408 (see, FIG. 4C) and an eligibility results icon corresponding to an eligibility results page 410 (see, FIG. 4D). The icons displayed on the progress tracker 402 will be highlighted once page related to that icon is displayed, such as episode information icon will be highlighted when an episode information page 404 is displayed.

The episode information page 404 of the interface 400 includes a physician name field 412, a National Provider Identifier (NPI) number field 414, an insurance name field 416, a Group ID field 418, a clinical episode field 420 and an estimated procedure date field 422. The physician name field 412 may be a text box where physician name can be entered manually using keyboard or a drop down menu where physician name can be selected from the list of physicians. The NPI number field 414 corresponds to a registered member of the episode management platform 118, for example, registered number of the episode initiator. The NPI field 414 is automatically filled by the episode management platform 118 when accessed by the physician. The insurance name field 416 may be a text box where name of an insurance service provider can be entered manually using keyboard or a drop down menu where insurance service provider name can be selected from a list of insurance service providers.

The Group ID field 418 may be a text box in which the physician may enter the Group ID details of the patient, such as Group ID of the patient 102 based on details in his/her primary insurance card. The clinical episode field 420 may be a text box where clinical episode corresponding to health issue, the patient is presenting with, can be entered manually using keyboard or a drop down menu where the clinical episode can be selected from the list of clinical episodes. The estimated procedure date field 422 may be a text box in which the physician may enter a procedure date for the clinical episode manually in a particular format or a date can be selected from a calendar that is displayed upon clicking the estimated procedure date field 422. The episode information page 404 of the interface 400 also includes a next tab 424 at bottom part of the page 404. When the physician accessing the interface 400 clicks on the next tab 424, the physician is presented with the patient information page 406. The patient information page 406 is explained in detail with reference to FIG. 4B.

FIG. 4B is an example representation of the patient information page 406 of the interface 400 for acquiring patient details, in accordance with an example embodiment. The patient details are acquired for performing an eligibility check of the patient for bundled payment when diagnosed for a clinical episode. The page 406 includes the progress tracker 402 and the patient information icon is highlighted to indicate the page 406 accessed by the physician. The page 406 includes a first name field 430, a middle name field 432, a last name field 434, a date of birth field 436, an insured member identifier field 438 and a primary diagnosis field 440. The first name field 430 may be a text box in which the physician may enter the first name of the patient. The middle name field 432 may be a text box in which the physician may enter middle name of the patient. It shall be noted that the middle name field 432 can be left blank in case the patient does not have the middle name. Similarly, the last name field 434 may be a text box in which the physician may enter the last name of the patient.

The physician can manually enter the birth date in the date of birth field 436 or select a date from a calendar displayed upon clicking the date of birth field 436. The insured member identifier field 438 may be a text box in which the physician may enter the insurance identifier of the patient from a primary insurance card associated with the patient. The primary diagnosis field 440 may be a text box where diagnosis details can be entered manually or the diagnoses can be selected from a drop down menu comprising a list of diagnosis. The page 406 includes the next tab 424 and clicking on the next tab 424 will navigate the physician to the page 408. The page 408 is explained in detail with reference to FIG. 4C.

FIG. 4C is an example representation of the confirmation page 408 of the interface 400 for confirming patient details such as to perform an eligibility check of the patient for bundled payment, in accordance with an example embodiment. The page 408 includes the progress tracker 402 and the confirmation icon is highlighted. The page 408 displays information about the patient collected at the pages 404 and 406, such as first name, middle name, last name, patient member id, NPI, date of birth, clinical episode name, physician name, group id, procedure date, insurance and primary diagnosis details. The page 408 includes a notes field 450 and a check eligibility tab 460. The notes field 450 is a text box in which the physician can enter remarks or comments regarding diagnosis or special instructions to be noted while performing the eligibility check. The check eligibility tab 460 will redirect the physician to the page 410 in which eligibility status of the patient is displayed. The page 410 is explained in detail with reference to FIG. 4D.

FIG. 4D is an example representation of the eligibility results page 410 of the interface 400 displaying eligibility check result for a patient, in accordance with an example embodiment. The page 410 includes the progress tracker 402 and the eligibility results icon is highlighted. The page 410 displays text indicating if the patient is eligible for the bundled payment.

As seen in FIG. 4D, the text indicates that the patient (John, M) is not eligible for bundled payment on a clinical episode. Therefore, the page 410 may also provide an option for the physician to view patient eligibility and financial information on the patient's major procedure. In such cases, with the patient's consent, the physician may check the patient's eligibility and patient responsibility for the surgical procedure alone (e.g., the knee replacement surgery) by clicking on a Yes tab 462. The physician can decline to view the patient's eligibility and the patient responsibility by clicking on a No tab 464. The page 410 includes a done tab 466 that the physician can click to close/complete the eligibility check of the patient on the interface 400. It shall be noted that the pages 404, 406, 408, 410 of the interface 400 have been shown for example purposes only and the interface 400 may have more or lesser fields than those depicted in the FIGS. 4A-4D.

FIG. 5A is a page 500 of an interface 500 displaying previous list of patient eligibility checks performed on the episode management platform 120, in accordance with an example embodiment. It shall be noted that the interface 500 described in FIG. 5A is accessible to a physician, such as the physician 104 on the user device 106. Similarly, a page 530 described with reference to FIG. 5B can also be accessed by the physician. The page 500 displays a search field 520 at top part of the page 500. The physician can search for a patient among a plurality of patients for whom eligibility checks were performed by providing a name of the patient in the search field 520.

Figure 5C:
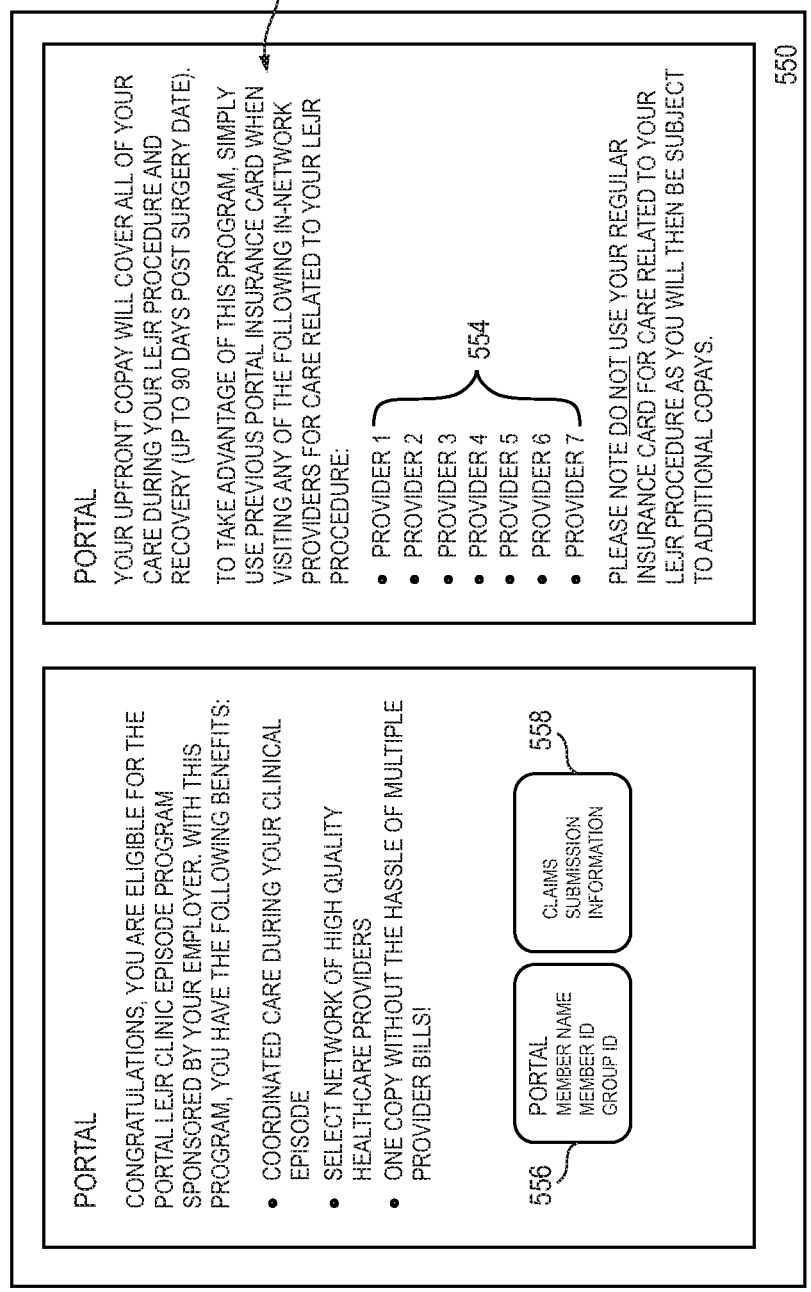
FIG. 5C is an example representation of an episode card generated by the episode management platform, in accordance with an example embodiment.

The page 500 includes a table displaying patient information and eligibility of that patient for bundled payment. The table includes headers such as, patient name 502, member ID 504, episode name 506, eligibility status 508, prior authorization (PA) status 510, claim initiation status 512 and actions 514. Each row of the table is provided with a check box and the physician can select a row of the table by clicking on the corresponding checkbox. As seen in FIG. 5A, a row 528 displays information corresponding to a patient, such as 'John, M' (patient name) with member ID W000000000 presenting with a clinical episode of knee replacement. The patient John is found to be eligible for bundled payment and requires prior authorization. The episode for the patient 'John, M' has already been initiated and the physician has been provided with options to check details of the clinical episode and eligibility details associated with the patient 'John, M' by clicking on a details tab 516. The physician can view a copy of the episode card by clicking on a card tab 518 that appears beside the details tab 516. The episode card can be downloaded and stored on a device (e.g., the device 106) associated with the physician. A copy of the episode card may be provided to the patient for accessing healthcare facilities from heath care service providers, such as, the healthcare service providers 114. It shall be noted that the card tab 518 will only be displayed when the patient is eligible for bundled payment. An example of the episode card is shown and explained with reference to FIG. 5C. The interface 500 also includes a check eligibility tab 522 at top part of the page 500 above the search field 520. In an example, clicking on the check eligibility tab 522, redirects the physician to a page 404 of the interface 400 to check eligibility of any patient.

FIG. 5B is a page 540 of the interface 500 displaying an example representation of eligibility details of the patient, in accordance with an example embodiment. The page 540 is displayed to the physician when he/she clicks on the details tab 516 (shown in FIG. 5A) of page 500. The page 540 displays eligibility details of the patient for the bundled payment of a clinical episode.

As seen in FIG. 5B, the page 540 displays patient details and eligibility details of the patient, such as, patient name, birth date of the patient, episode name, bundled payment process status, physician name, initiator name, prior authorization required status, coinsurance amount, payor type, copay amount, deductible, patient responsibility, major procedure date and a checked date.

The patient name 'John, M' is same as name provided by the physician in the fields 430, 432 and 434. The birth date of the patient (Jan. 25, 1970) is as provided by the physician in the date of birth field 436 and episode name is as provided by the physician in the clinical episode field 420. The physician name is as provided by the physician in the physician name field 412. The physician is usually the initiator of the clinical episode and the physician's name is provided as the initiator. The bundled payment process status indicates if the bundled payment process for the clinical episode has been initiated and the PA required status indicates if a prior authorization is required for the patient.

It shall be noted that insurance details of the patient are retrieved to display information, such as, payor type, deductible, coinsurance, copay and patient responsibility in the page 540. The payor type indicates if the insurance payment is by a health plan payor scheme or an employee carve-out scheme. A health plan payor scheme is one that requires the bundled payment to be submitted via their standard claims adjudication process, whereas an employer carve-out scheme requires the bundled payment claim to be billed to the employer via an invoice process. The deductible indicates an amount that has to be paid by the patient prior to the insurance service provider (payor) paying for any healthcare services availed by the patient. Coinsurance refers to a percentage amount payable by the patient after paying a deductible towards expenses for the healthcare services availed by the patient. Copay is a fixed amount payable by the patient to the insurance service provider for availing the bundled payment that covers the clinical episode of the patient. The patient responsibility indicates the amount payable by the patient apart from the expenses covered by the bundled payment of the insurance service provider. For example, the patient responsibility will be an aggregation of the deductible, coinsurance amount and copay amount. The major procedure date displays a date at which major treatment, for example, a knee replacement surgery will be performed and a checked date indicates date on which the eligibility check was performed on the patient.

FIG. 5C is a schematic representation of an episode card 550 generated by the interface 500 is illustrated, in accordance with an example embodiment. The episode card 550 comprises information about the patient and the details 556 for submitting claims to the claim adjudication system 122 (see, FIGS. 4A-4D, 5A-5B).

As seen in FIG. 5C, the episode card 550 displays text 552 indicating terms and services offered for the patient in possession of the episode card 550. The episode card 550 also includes a list of healthcare service providers 554 (provider 1, provider 2, provider 3, provider 4, provider 5, provider 6, and provider 7) to whom the patient in possession of the episode card 550 can visit and avail healthcare services for the clinical episode. The healthcare service providers 554 are from a network of service providers who provide healthcare services for patients based on the episode card 550 and avail estimated payment for the healthcare service by submitting claims to the claim adjudication system 122. It shall be noted that the healthcare service providers (provider 1, provider 2, provider 3, provider 4, provider 5, provider 6, and provider 7) can be a healthcare facility (e.g., the hospital facility 108) or healthcare service provider (e.g., the healthcare service providers 114). The episode card 550 also includes patient details and claim adjudication details 556, such as member name (patient name), member ID and group ID.

Figure 6A:
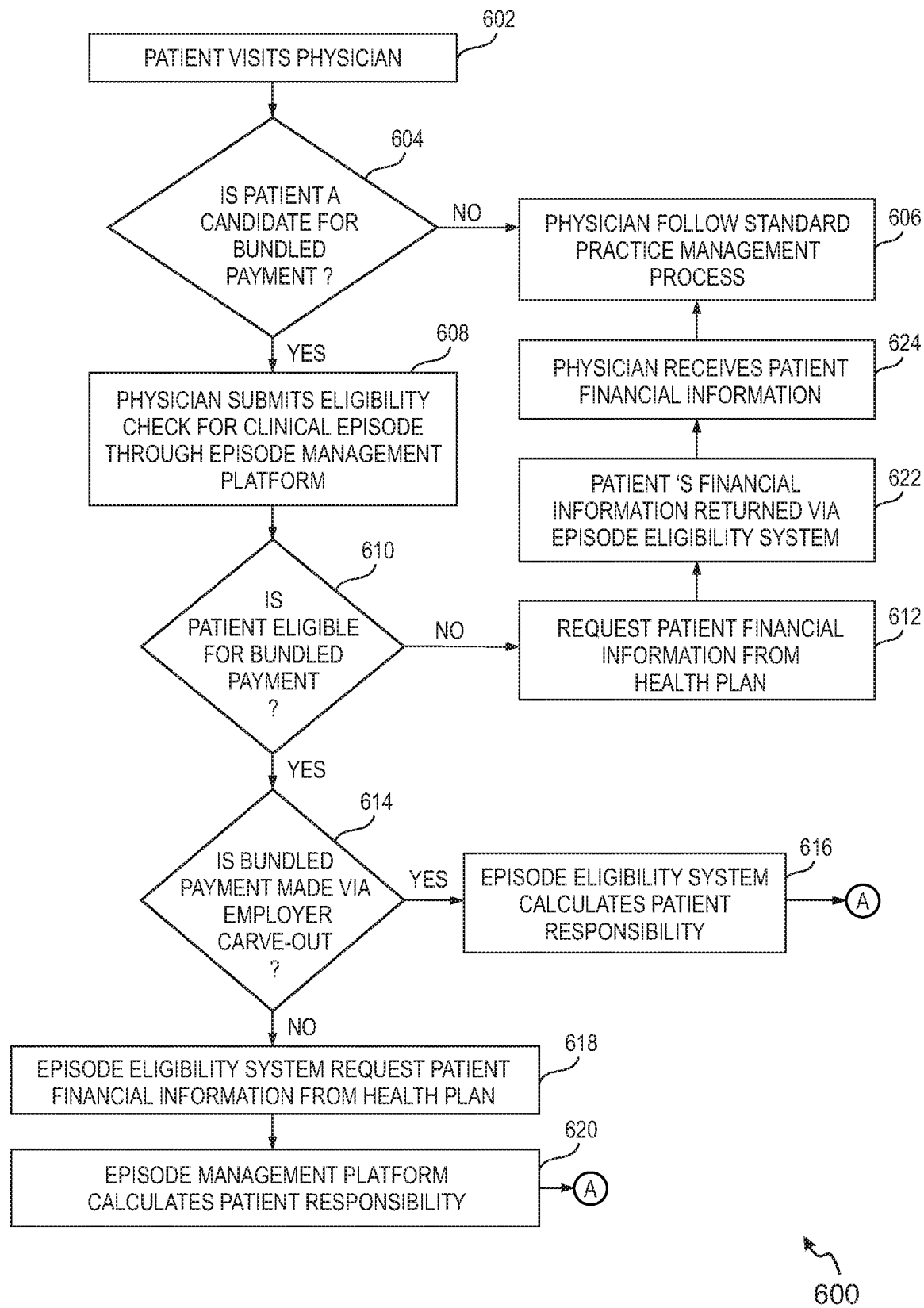
FIGS. 6A and 6B is an example flow diagram of a method for bundled payment adjudication, in accordance with an example embodiment.
Figure 6B:
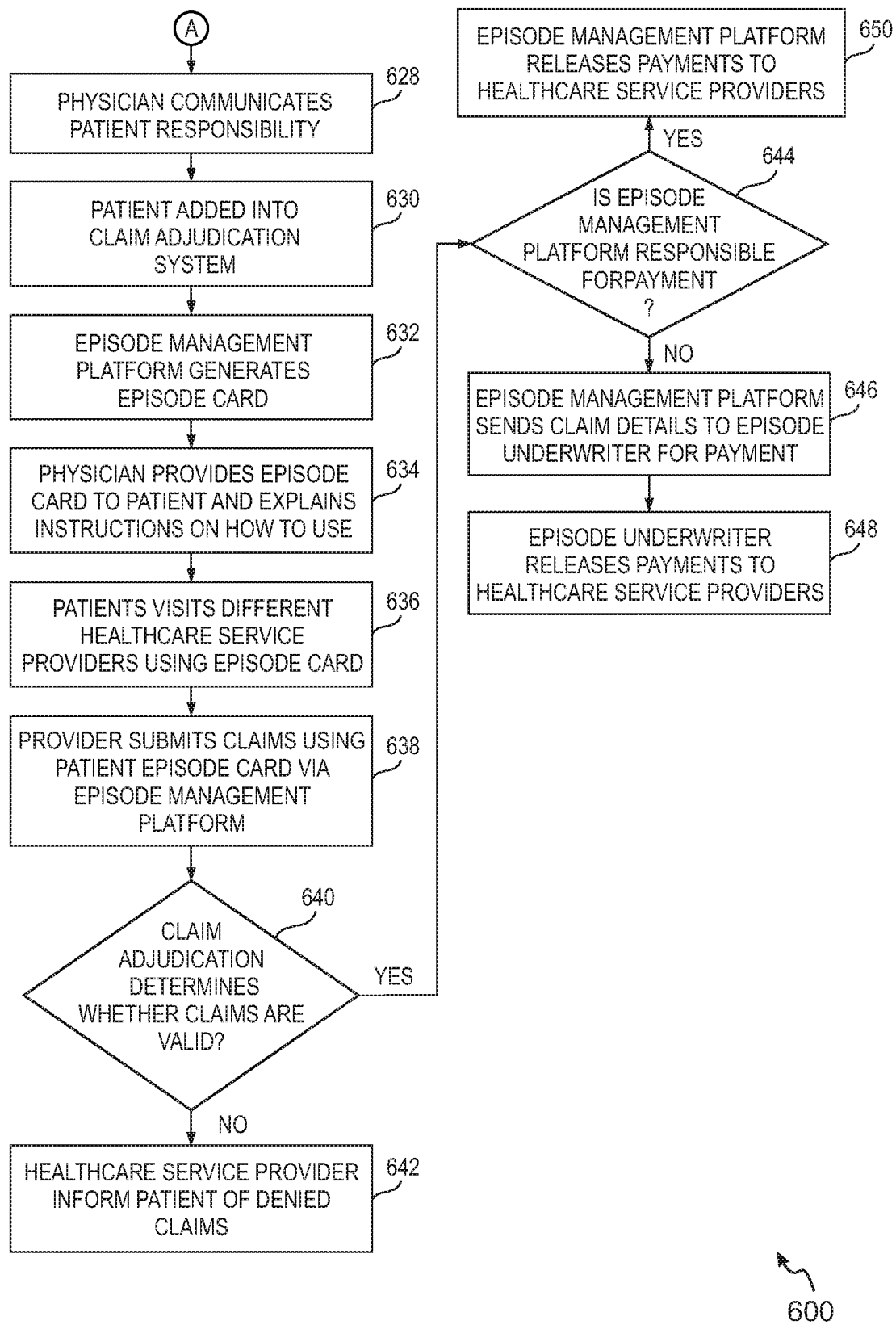

FIGS. 6A and 6B are example flow diagrams of a method 600 for bundled payment adjudication, in accordance with an example embodiment. The sequence of operations of the method 600 need not be necessarily executed in the same order as they are presented. Further, one or more operations may be grouped together and performed in form of a single step, or one operation may have several sub-steps that may be performed in parallel or in sequential manner.

At operation 602, a patient (e.g., the patient 102) visits a physician (also referred to as 'episode initiator') in a hospital facility to consult with the physician for a health issue he/she is facing.

At operation 604, the physician checks whether the patient is a candidate for the bundled payment process. For instance, the physician diagnoses health condition of the patient and based on the diagnosis, the physician determines if the patient needs to opt for the bundled payment. In an example, if the patient presents with symptoms of viral fever, the health condition may not require hospitalization or therapies from healthcare service providers. The expenses of medical treatment provided for the medical condition can be paid by the patient and/or the insurance service provider. Alternatively, if the physician diagnoses a health condition such as atherosclerosis that may require hospitalization and extensive treatment such as visiting two or more healthcare service providers, the physician may advise the patient to opt for bundled payment. It shall be noted that the patient will be a candidate for bundled payment only if the physician determines that the health condition of the patient requires extended care and healthcare service over a time period. If the patient is a candidate for bundled payment, operation 608 is performed else operation 606 is performed.

At operation 606, if the patient is not a candidate for the bundled payment, the physician follows a standard practice management process for treating the patient. At operation 608, if the patient is the candidate for the bundled payment, the physician submits an eligibility check for a clinical episode associated with the patient via an episode eligibility system of the episode management platform. For instance, patient information associated with the patient are provided and checked if the patient is eligible for bundled payment. The patient information includes but is not limited to a patient identifier, a clinical episode associated with the patient, and a primary health insurance information associated with the patient. This requires the physician to log on to an interface (see, interface 400) provided by the episode management platform (e.g., the episode management platform 120) for performing an eligibility check. The results of the eligibility check for the patient presenting with the clinical episode provide detailed information on patient eligibility and patient responsibility for the clinical episode. Submitting patient and insurance details for performing the eligibility check has been explained in detail with reference to FIGS. 4A-4D.

At operation 610, the episode management platform determines if the patient is eligible for bundle payment of claims for the clinical episode based on the stored eligibility file of the patient. The eligibility file is obtained from the insurance service provider or the employer group of the patient.

In an example, if the patient requires a knee surgery, the physician submits the eligibility check with patient information to determine the patient's eligibility for the clinical episode. For example, the episode eligibility system of the episode management platform checks if the insurance service provider of the patient covers the bundled payment for a particular clinical episode. If the episode management platform determines that the patient is eligible for bundle payment for the clinical episode, operation 614 is performed else operation 612 will be performed.

At operation 614, the episode management platform checks if the bundle payment for the clinical episode will be paid via an employer carve-out scheme. If the bundle payment for the clinical episode is paid via the employer carve-out scheme, then operation 616 is performed else operation 618 will be performed.

At operation 616, the episode eligibility system 120 calculates the patient responsibility based upon payment rules defined by the employer.

At operation 618, the episode eligibility system 120 requests financial information associated with the patient from the health plan by sending a financial information request to the insurance service provider of the patient.

At operation 620, the episode eligibility system 120 calculates the patient responsibility. The patient responsibility is determined based on the financial information of the patient retrieved from the health plan. The patient responsibility is determined at least based on a deductible amount, coinsurance amount and a copay amount. An example of a UI of the episode eligibility system 120 displaying the patient responsibility is shown and explained with reference to FIG. 5B.

In an example, if a contracted payment rate on a hip replacement with an insurance company is $20,000, a remaining deductible for the patient is $4,000 (of $5,000 deductible) with coinsurance of 20% on amount above deductible and an out-of-pocket (OOP) max of $10,000, then the patient responsibility would be:

Remaining Deductible: $4,000

Coinsurance: Total Claim $20,000 less Remaining Deductible $4,000=$16,000*20% of $16,000=$3,200

Total Patient Responsibility: Deductible $4,000+Coinsurance $3,200=$7,200

In an example, the Total Patient Responsibility is compared to OOP max to see if OOP max applies: Previously Used Deductible: $1,000+calculated total patient responsibility on bundled payment: $7,200=$8,200 which is less than $10,000 OOP max, so Patient Responsibility on Total Bundle is $7,200.

In an example, if OOP max was $7,500, then Patient Responsibility would be $6,500.

As previously Used Deductible: $1,000 plus calculated on Bundle: $7,200=$8,200 which is more than $7,500 OOP max, so recalculate by taking OOP max of $7,500 and subtract Previously Used Deductible of $1,000

At operation 612, the patient's financial information is requested from the insurance service provider. At operation 622, the episode eligibility system 120 returns the patient's financial information, including remaining deductible, remaining OOP, coinsurance and copay. The financial information is displayed on a UI of a device (e.g., the device 106) associated with the physician via the episode management platform 120.

At operation 624, the physician receives the patient's financial information and follows the standard practice management process for treating the patient.

At operation 628, the physician communicates the estimated patient responsibility to the patient. For example, the physician communicates the amount he/she has to pay for availing healthcare services under the bundled payment. At operation 630, after knowing the patient responsibility for availing bundled payment, if the patient wishes to opt for the bundled payment, the physician initiates the episode. At that time, the patient is added to the claim adjudication system 122 for the bundled payment.

At operation 632, the episode card is generated by the episode management platform 118. The episode card includes the patient information, plan information, validity details and list of network healthcare service providers. The patient can use the episode card to avail healthcare facilities at any healthcare service provider pursuant to the episode card's list of healthcare service providers. An example of the episode card is shown and explained with reference to FIG. 5C.

At operation 634, the physician will download the episode card from the episode management platform 118 and will provide the episode card to the patient. The physician may also explain benefits of the episode card and provide instructions to the patient on how the episode card can be used.

At operation 636, the patient visits one or more healthcare service providers (e.g., the healthcare service providers 114) for availing healthcare services by displaying the episode card. For example, a patient diagnosed with knee injury may avail hospital facilities for surgery and post-operative recovery at a hospital X and receive physiotherapy sessions from a physiotherapy clinic Y. The patient avails the healthcare service from the hospital X and the physiotherapy clinic Y by displaying the episode card generated by the episode management platform 118.

At operation 638, the one or more healthcare service providers submit one or more claims for the one or more healthcare services availed by the patient using the episode card to the claim adjudication system 122. For example, the hospital X and the physiotherapy clinic Y submit claims comprising estimated cost for services availed by the patient to the claim adjudication system 122.

At operation 640, the claim adjudication system 122 of the episode management platform 118 checks whether the claims submitted by the healthcare service providers are valid claims or invalid claims based on a set of episode definition parameters.

At operation 642, if the claims are found to be invalid claims, the episode management platform 118 generates a notification for the patient and the healthcare service provider related to the invalid claim. The notification may include reasons for classifying the claim as the invalid claim and an invalid claim payment amount to be paid by the patient to the health care service provider associated with the invalid claim. The healthcare service provider may inform the patient about the denied status of the claims, at which time the healthcare service provider would need to submit the claim using the patient's primary insurance card. For example, if the patient had availed services of a cardiologist while consulting for the clinical episode of knee surgery, the patient eligibility for bundled payment determined for the clinical episode of knee surgery may not include cardiology services and hence be denied. The invalid claims may be covered by the insurance service provider and the healthcare service provider may use the primary insurance card of the patient to raise claims for the denied claims in the bundled payment.

At operation 644, if the claims are found to be valid claims, the claim adjudication system 122 determines whether the episode management platform 118 is responsible for payment or not. At operation 650, if the episode management platform 118 is found to be responsible for payment, the episode management platform 118 releases payments to the healthcare service providers.

At operation 646, if the episode management platform 118 is not responsible for payment of the bundle payment, the episode management platform 118 sends claim details of the healthcare service providers to the episode underwriter for releasing the payment. At operation 648, the episode underwriter releases payments for the healthcare service providers.

Figure 7:
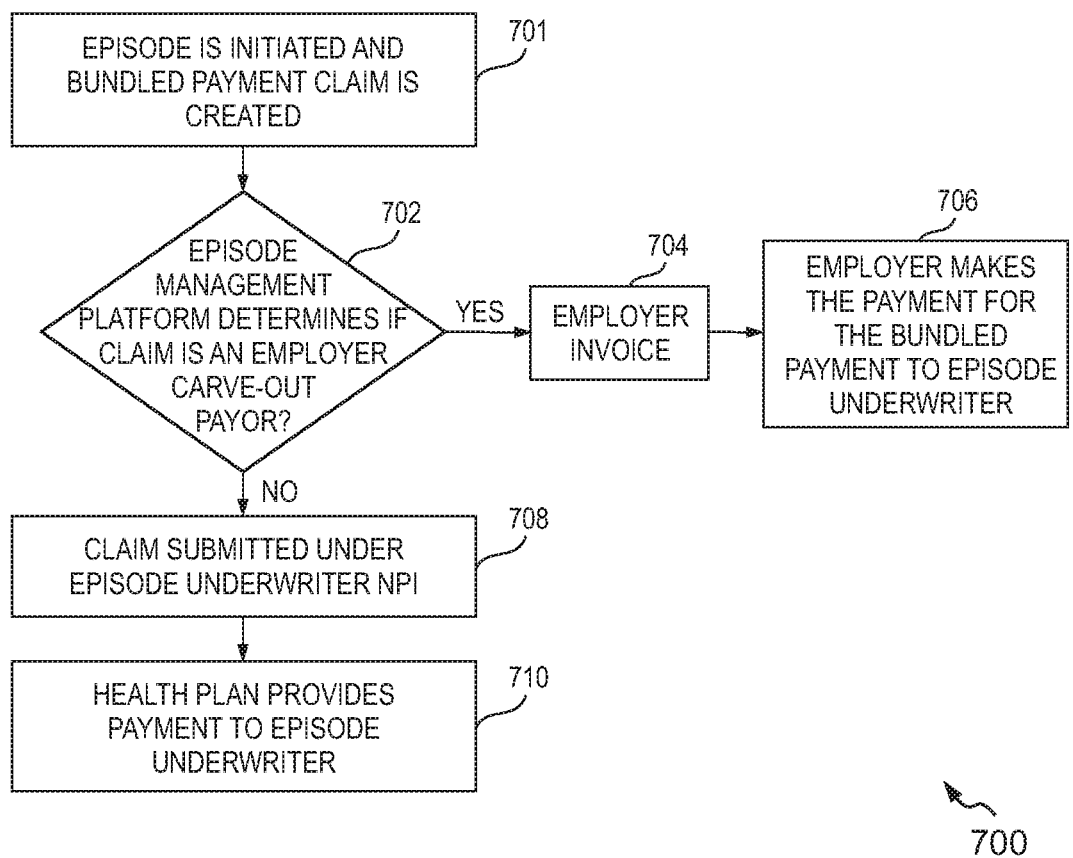
FIG. 7 is a flow diagram of a method for releasing bundled payments to an episode underwriter in case of employer carve-out and health plan, in accordance with an example embodiment.

FIG. 7 is a flow diagram of an example method 700 for releasing bundled payments to the episode underwriter 124 in case of the employer group carve-out scheme and the health plan payor scheme, in accordance with an example embodiment. The operations of the method 700 may be performed by an episode management platform (e.g., the episode management platform) residing at a server (e.g., the server 112). The sequence of operations of the method 700 need not be necessarily executed in the same order as they are presented. Further, one or more operations may be grouped together and performed in form of a single step, or one operation may have several sub-steps that may be performed in parallel or in sequential manner.

At operation 701, the patient's episode is initiated and the bundled payment claim is created within the episode management platform 118. For instance, the eligibility of the patient for bundled payment and patient responsibility is determined based on the eligibility information. When the patient agrees to pay the patient responsibility, an episode is created for the bundled payment for the clinical episode and the patient is added to the claim adjudication system of the episode management platform.

At operation 702, the episode management platform 118 determines whether the bundled payment claim is for a health plan payor or for an employer group carve-out payor. In case of employer carve-out payor, the bundled payment claim is queued in the episode management platform 118 for invoicing to the employer of the patient. If the bundled payment claim is related to the employer group carve-out, then operation 704 will be performed else operation 708 will be performed.

At operation 704, the employer group is invoiced for the bundled payment claim by an episode underwriter (e.g., the episode underwriter 124). A claim payment request including payment information associated with the bundled payment claim is sent to the employer. The payment information includes a payment amount for the health care service, a payment mode, and an account information of the episode underwriter. At operation 706, the employer makes payment for payment amount associated with the bundled payment to the episode underwriter.

At operation 708, the bundled payment claim is submitted using the episode underwriter NPI directly to the insurance service provider. At operation 710, the health plan provider (e.g., the insurance service provider 116) pays the requested amount to the episode underwriter.

Figure 8:
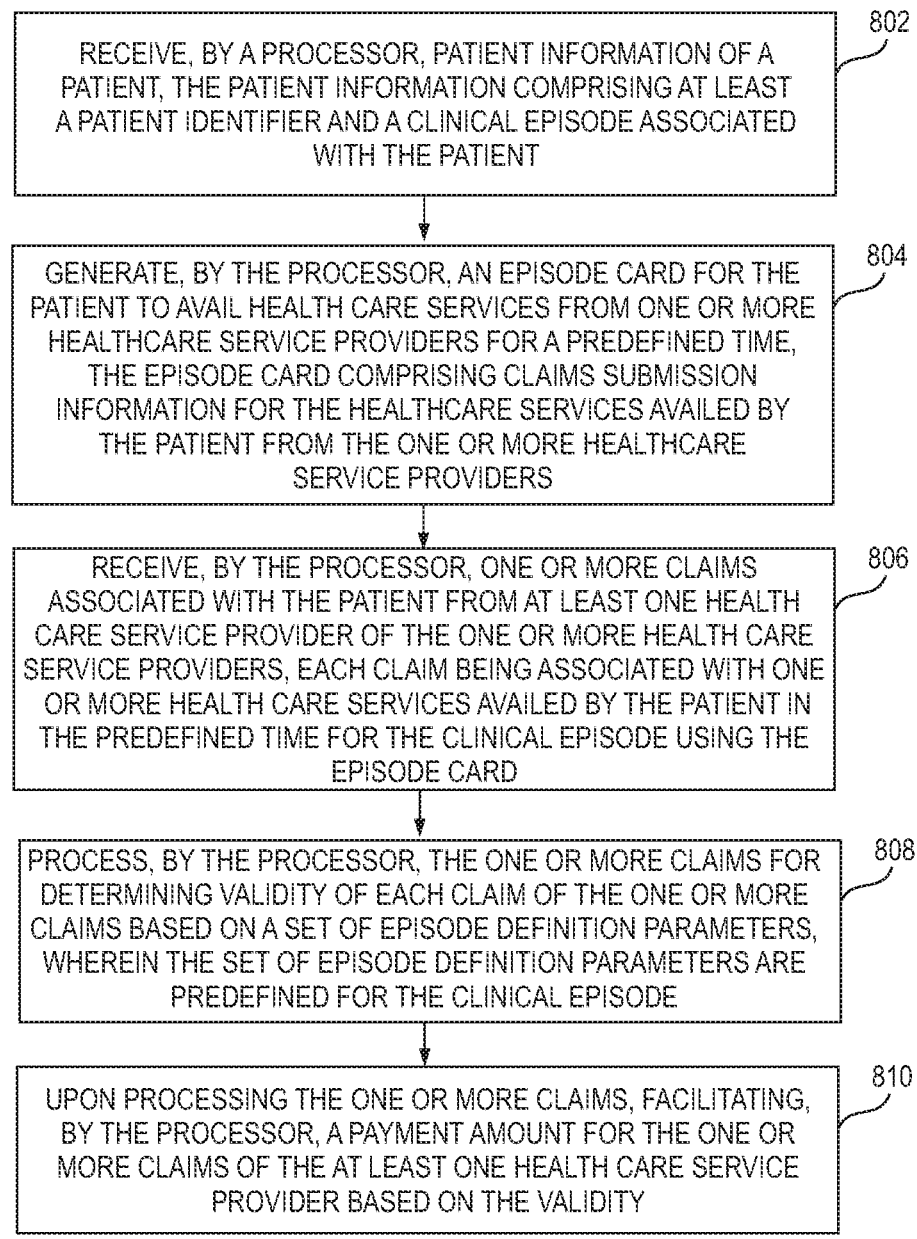
FIG. 8 is a flow diagram of a method for bundled payment adjudication for healthcare services, in accordance with an example embodiment.

FIG. 8 is a flowchart of a computer implemented method 800 for bundled payment adjudication, in accordance with another example embodiment. The operations of the method 800 may be carried out by a server such as the server 112, the system 300 or the device 106. The sequence of operations of the method 800 may not be necessarily executed in the same order as they are presented. Further, one or more operations may be grouped together and performed in form of a single step, or one operation may have several sub-steps that may be performed in parallel or in sequential manner.

At operation 802, the method 800 includes receiving, by a processor, patient information of a patient. The patient information is provided by a healthcare service provider (e.g., the physician 104) after diagnosing health condition of the patient. The patient information includes at least a patient identifier (ID) and a clinical episode associated with the patient. The patient may visit the physician for an illness and the physician may analyse a health condition of the patient to determine a clinical episode. Accordingly, if the physician diagnoses the health condition to require an extended hospitalization, he/she may access an application, for example, the episode management platform for providing patient specific details (the patient information).

At operation 804, the method 800 includes generating, by the processor, an episode card for the patient to avail health care services from one or more healthcare service providers for a predefined time. The episode card includes claim submission information for the healthcare services availed by the patient from the one or more healthcare service providers. If the patient is found eligible for the bundled payment, the episode card is generated. The eligibility of a patient is determined using eligibility information of the patient based an eligibility file provided by an insurance service provider or an employer group. The eligibility files may be EDI 834 files, CSV files or some other type of automated feed or API. The eligibility files provide eligibility information of the patient that may be used by the episode eligibility system to determine the patient's eligibility for bundled payment relating to a particular clinical episode. The eligibility file includes health insurance details of the patient. In an embodiment, the episode management platform includes an episode eligibility system that analyses the eligibility information to determine if the patient is eligible for bundled payment for that specific clinical episode. If the patient is found eligible, the generated episode card can be used by the patient to avail healthcare services from the one or more healthcare service providers within the predefined time for the clinical episode. However, it shall be noted that expenses arising out of any other health care service availed by the patient that may not be included in the bundled payment (e.g., health care services other than the clinical episode) may not be availed using the episode card. The predefined time is a validity period (e.g., 90 days) of the episode card and is mentioned as the validity information on the generated episode card.

At operation 806, the method 800 includes receiving, by the processor, one or more claims associated with the patient from at least one health care service provider of the one or more health care service providers. Each claim is associated with one or more health care services availed by the patient in the predefined time for the clinical episode using the episode card. For instance, the patient may have undergone the knee replacement surgery and availed post operative care from health care provider A for $1000 using the episode card. Later, the patient may have regularly visited a physiotherapist at the health care service provider B and availed physiotherapy services for $500 using the episode card for the clinical episode of knee replacement. Additionally, the patient may have visited the health care service provider C for availing cardiology services worth $500. The health care service provider A, health care service provider B and the health care service provider C will each raise a claim for $1000, $500 and $500, respectively.

At operation 808, the method 800 includes processing, by the processor, the one or more claims for determining the validity of each claim of the one or more claims based on a set of episode definition parameters. The set of episode definition parameters are predefined for the clinical episode. The episode definition parameters such as, procedures, valid diagnoses, valid health care provider network, episode lengths and episode start for a clinical episode are provided by the episode underwriter. Each claim is classified as a valid claim or an invalid claim based on the episode definition parameters. For instance, the claims raised by each of the healthcare service providers for each service availed by the patient is compared against the episode definition parameters of the clinical episode as determined by the episode management platform to determine healthcare services that are covered by the bundled payment for the clinical episode. For instance, in a clinical episode of knee replacement created for the patient, the claim raised by the health care service provider A for surgery charges and post operative care is classified as a valid claim and the claim raised by the health care service provider B for physiotherapy is also classified as valid claim as these are procedures covered by the bundled payment. However, cardiology services availed at the health care service provider C using the episode card is classified as an invalid claim as the episode definition parameters for knee replacement do not cover cardiology services. The claim raised by the health care service provider C is denied and the health care service provider C is notified of the invalid claim.

At operation 810, the method 800 includes upon processing the one or more claims, facilitating, by the processor, a payment amount for the one or more claims of the at least one health care service provider based on the validity.

Figure 9:
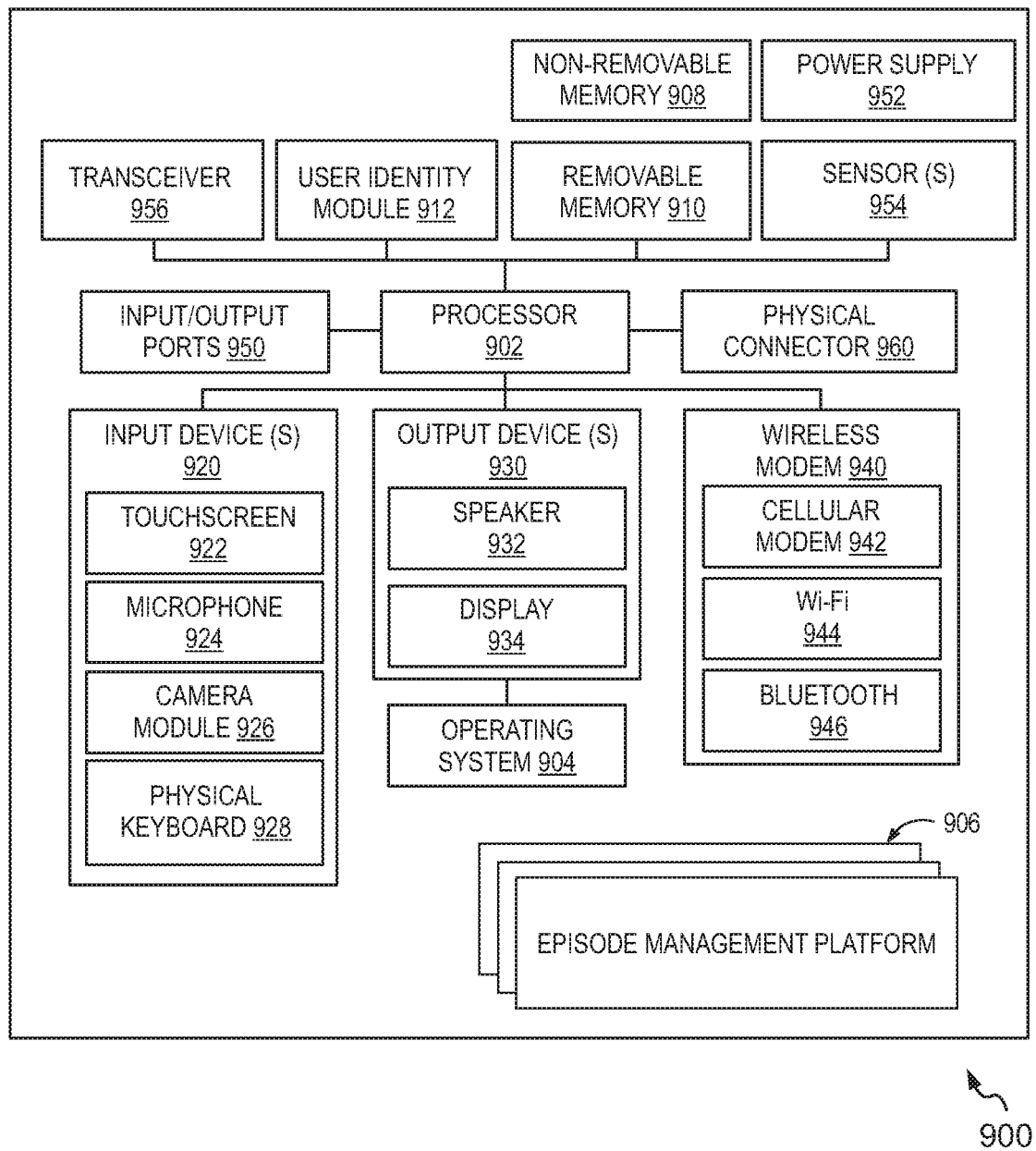
FIG. 9 is a block diagram of a user device, in accordance with an example embodiment.

FIG. 9 shows a simplified block diagram of an electronic device 900 capable of implementing the various embodiments of the present disclosure. The electronic device 900 may be an example of the device 106. In an embodiment, the various operations related to bundled payment adjudication can be facilitated using an episode management platform installed in the electronic device 900. It should be understood that the electronic device 900 as illustrated and hereinafter described is merely illustrative of one type of device and should not be taken to limit the scope of the embodiments. As such, it should be appreciated that at least some of the components described below in connection with that the electronic device 900 may be optional and thus in an example embodiment may include more, less or different components than those described in connection with the example embodiment of the FIG. 9. As such, among other examples, the electronic device 900 could be any of a mobile electronic device or may be embodied in any of the electronic devices, for example, cellular phones, tablet computers, laptops, mobile computers, personal digital assistants (PDAs), mobile televisions, mobile digital assistants, or any combination of the aforementioned, and other types of communication or multimedia devices.

The illustrated electronic device 900 includes a controller or a processor 902 (e.g., a signal processor, microprocessor, ASIC, or other control and processing logic circuitry) for performing such tasks as signal coding, data processing, image processing, input/output processing, power control, and/or other functions. An operating system 904 control the allocation and usage of the components of the electronic device 900 and support for one or more applications programs (see, the episode management platform 118) that implements one or more of the innovative features described herein. The applications 906 may include the episode management platform and common mobile computing applications (e.g., telephony applications, email applications, calendars, contact managers, web browsers, messaging applications such as USSD messaging or SMS messaging or SIM Tool Kit (STK) application) or any other computing application. The episode management platform is configured to be in operative communication with other applications for example, through the OS or using API Calls, for facilitating bundled payment adjudication for healthcare services.

The illustrated electronic device 900 includes one or more memory components, for example, a non-removable memory 908 and/or a removable memory 910. The non-removable memory 908 and/or the removable memory 910 may be collectively known as database in an embodiment. The non-removable memory 908 can include RAM, ROM, flash memory, a hard disk, or other well-known memory storage technologies. The removable memory 910 can include flash memory, smart cards, or a Subscriber Identity Module (SIM). The one or more memory components can be used for storing data such as, eligibility files of a plurality of patients, claim requests and/or code for running the operating system 904 and the episode management platform. The electronic device 900 may further include a user identity module (UIM) 912. The UIM 912 may be a memory device having a processor built in. The UIM 912 may include, for example, a subscriber identity module (SIM), a universal integrated circuit card (UICC), a universal subscriber identity module (USIM), a removable user identity module (R-UIM), or any other smart card. The UIM 912 typically stores information elements related to a mobile subscriber. The UIM 912 in form of the SIM card is well known in Global System for Mobile Communications (GSM) communication systems, Code Division Multiple Access (CDMA) systems, or with third-generation (3G) wireless communication protocols such as Universal Mobile Telecommunications System (UMTS), CDMA9000, wideband CDMA (WCDMA) and time division-synchronous CDMA (TD-SCDMA), or with fourth-generation (4G) wireless communication protocols such as LTE (Long-Term Evolution).

The electronic device 900 can support one or more input devices 920 and one or more output devices 930. Examples of the input devices 920 may include, but are not limited to, a touch screen/a display screen 922 (e.g., capable of capturing finger tap inputs, finger gesture inputs, multi-finger tap inputs, multi-finger gesture inputs, or keystroke inputs from a virtual keyboard or keypad), a microphone 924 (e.g., capable of capturing voice input), a camera module 926 (e.g., capable of capturing still picture images and/or video images) and a physical keyboard 928. Examples of the output devices 930 may include but are not limited to a speaker 932 and a display 934. Other possible output devices can include piezoelectric or other haptic output devices. Some devices can serve more than one input/output function. For example, the touch screen 922 and the display 934 can be combined into a single input/output device.

A wireless modem 940 can be coupled to one or more antennas (not shown in the FIG. 9) and can support two-way communications between the processor 902 and external devices, as is well understood in the art. The wireless modem 940 is shown generically and can include, for example, a cellular modem 942 for communicating at long range with the mobile communication network, a Wi-Fi compatible modem 944 for communicating at short range with an external Bluetooth-equipped device or a local wireless data network or router, and/or a Bluetooth-compatible modem 946. The wireless modem 940 is typically configured for communication with one or more cellular networks, such as a GSM network for data and voice communications within a single cellular network, between cellular networks, or between the electronic device 900 and a public switched telephone network (PSTN).

The electronic device 900 can further include one or more input/output ports 950, a power supply 952, one or more sensors 954 for example, an accelerometer, a gyroscope, a compass, or an infrared proximity sensor for detecting the orientation or motion of the electronic device 900, a transceiver 956 (for wirelessly transmitting analog or digital signals) and/or a physical connector 960, which can be a USB port, IEEE 1294 (FireWire) port, and/or RS-232 port. The illustrated components are not required or all-inclusive, as any of the components shown can be deleted and other components can be added.

FIG. 10 illustrates a block diagram of a server 1000, which may be an example of the server 112, in accordance with an embodiment of the present disclosure. The server 1000 includes a computer system 1002 and one or more databases.

The computer system 1002 includes a processor 1006 for executing instructions. Instructions may be stored in, for example, but not limited to, a memory 1008. The processor 1006 may include one or more processing units (e.g., in a multi-core configuration). The processor 1006 is operatively coupled to a communication interface 1010 and an episode management platform 1004. The processor 1006 may also be operatively coupled to a database 1004. The database 1004 is any computer-operated hardware suitable for storing and/or retrieving data such as, episode definition parameters for a particular clinical episode. The database 1004 is also configured to store eligibility data file feeds of a plurality of members. The eligibility data file feeds may take the form of EDI 834 files, CSV files or some other type of automated feed or API. The database 1004 may include multiple storage units such as hard disks and/or solid-state disks in a redundant array of inexpensive disks (RAID) configuration. The database 1004 may include, but not limited to, a storage area network (SAN) and/or a network attached storage (NAS) system or cloud storage. In some alternate embodiments, the database 1004 may also include magnetic storage devices (such as hard disk drives, floppy disks, magnetic tapes, etc.), optical magnetic storage devices (e.g., magneto-optical disks), semiconductor memories (such as mask ROM, PROM (programmable ROM), EPROM (erasable PROM), Phase-change memory, flash ROM, RAM (random access memory)), etc.

In some embodiments, the database 1004 is integrated within computer system 1002. For example, computer system 1002 may include one or more hard disk drives as database 1004. In other embodiments, database 1004 is external to computer system 1002 and may be accessed by the computer system 1002 using a storage interface 1012. The storage interface 1012 is any component capable of providing the processor 1006 with access to the database 1004. The storage interface 1012 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 1006 with access to the database 1004.

The memory 1008 is a storage device embodied as one or more volatile memory devices, one or more non-volatile memory devices, and/or a combination of one or more volatile memory devices and non-volatile memory devices, for storing micro-contents information and instructions. The memory 1008 may be embodied as magnetic storage devices (such as hard disk drives, floppy disks, magnetic tapes, etc.), optical magnetic storage devices (e.g., magneto-optical disks), CD-ROM (compact disc read only memory), CD-R (compact disc recordable), CD-R/W (compact disc rewritable), DVD (Digital Versatile Disc), BD (Blu-ray® Disc), and semiconductor memories (such as mask ROM, PROM (programmable ROM), EPROM (erasable PROM), flash ROM, RAM (random access memory), etc.).

The episode management platform 1014 is an example of the episode management platform 118 explained with reference to FIG. 1. The episode management platform 1014 may be embodied within the computer system 1002 and includes an episode eligibility system and a claim adjudication system (not shown in FIG. 10) for managing bundled payment of claims for a clinical episode of care. The processor 1006 interacts with the episode management platform 118 to operate the episode eligibility system and the claim adjudication system. The episode eligibility system determines the eligibility of a patient for bundled payment of claims for a particular clinical episode of care and if the patient is found to be eligible then the episode eligibility system adds the patient to the claim adjudication system. The claim adjudication system manages the payments of healthcare service providers whose services are used by the patient during the clinical episode of care.

The server 1000 as illustrated and hereinafter described is merely illustrative of a system that could benefit from embodiments of the invention and, therefore, should not be taken to limit the scope of the invention. It may be noted that the server 1000 may include fewer or more components than those depicted in FIG. 10. As explained above, the server 1000 may be included within or embody an electronic device. Moreover, the server 1000 may be implemented as a centralized system, or, alternatively, the various components of server 1000 may be deployed in a distributed manner while being operatively coupled to each other.

Various example embodiments disclosed herein provide an episode eligibility system that determines eligibility of a patient for the bundled payment. Further, the episode eligibility system receives eligibility files from the insurance service providers for only those members who are eligible, and further determines patient responsibility for the treatment of a clinical episode. This ensures that the patient can opt for an informed decision of cost incurred in performing a procedure or for availing healthcare services. Additionally, the episode definitions are easily created and customized based upon the relevant diagnoses, procedures, network providers and length of episodes. Each episode definition is tailored for that specific episode, hence only relevant claims for that episode are adjudicated and gets paid, and rest all claims that do not meet the definition are denied. Moreover, the patient receives an episode card for bundled payment that can be used during the entire clinical episode at different healthcare service providers thereby reducing hassles of the patient while availing healthcare services from different healthcare service providers. The claims for the healthcare services availed by the patient are submitted by each healthcare provider to the episode management platform that resolve the validity of claims and settle the amount payable to each healthcare service provider based on the valid claims.

The disclosed systems and methods with reference to FIGS. 1 to 10, or one or more operations of the flow diagrams 600, 700 and 800 may be implemented using software including computer-executable instructions stored on one or more computer-readable media (e.g., non-transitory computer-readable media, such as one or more optical media discs, volatile memory components (e.g., DRAM or SRAM), or non-volatile memory or storage components (e.g., hard drives or solid-state non-volatile memory components, such as Flash memory components) and executed on a computer (e.g., any suitable computer, such as a laptop computer, net book, Web book, tablet computing device, smart phone, or other mobile computing device). Such software may be executed, for example, on a single local computer or in a network environment (e.g., via the Internet, a wide-area network, a local-area network, a remote web-based server, a client-server network (such as a cloud computing network), or other such network) using one or more network computers. Additionally, any of the intermediate or final data created and used during implementation of the disclosed methods or systems may also be stored on one or more computer-readable media (e.g., non-transitory computer-readable media) and are considered to be within the scope of the disclosed technology. Furthermore, any of the software-based embodiments may be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

Although the invention has been described with reference to specific exemplary embodiments, it is noted that various modifications and changes may be made to these embodiments without departing from the broad spirit and scope of the invention. For example, the various operations, blocks, etc., described herein may be enabled and operated using hardware circuitry (for example, complementary metal oxide semiconductor (CMOS) based logic circuitry), firmware, software and/or any combination of hardware, firmware, and/or software (for example, embodied in a machine-readable medium). For example, the apparatuses and methods may be embodied using transistors, logic gates, and electrical circuits (for example, application specific integrated circuit (ASIC) circuitry and/or in Digital Signal Processor (DSP) circuitry).

The present disclosure is described above with reference to block diagrams and flowchart illustrations of method and system embodying the present disclosure. It will be understood that various block of the block diagram and flowchart illustrations, and combinations of blocks in the block diagrams and flowchart illustrations, respectively, may be implemented by a set of computer program instructions. These set of instructions may be loaded onto a general-purpose computer, special purpose computer, or other programmable data processing apparatus to cause a device, such that the set of instructions when executed on the computer or other programmable data processing apparatus create a means for implementing the functions specified in the flowchart block or blocks. Although other means for implementing the functions including various combinations of hardware, firmware and software as described herein may also be employed.

Various embodiments described above may be implemented in software, hardware, application logic or a combination of software, hardware and application logic. The software, application logic and/or hardware may reside on at least one memory, at least one processor, an apparatus or, a non-transitory computer program product. In an example embodiment, the application logic, software or an instruction set is maintained on any one of various conventional computer-readable media. In the context of this document, a "computer-readable medium" may be any non-transitory media or means that can contain, store, communicate, propagate or transport the instructions for use by or in connection with an instruction execution system, apparatus, or device, such as a computer. A computer-readable medium may comprise a computer-readable storage medium that may be any media or means that can contain or store the instructions for use by or in connection with an instruction execution system, apparatus, or device, such as a computer.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The embodiments were chosen and described in order to best explain the principles of the present disclosure and its practical application, to thereby enable others skilled in the art to best utilize the present disclosure and various embodiments with various modifications as are suited to the particular use contemplated. It is understood that various omissions and substitutions of equivalents are contemplated as circumstance may suggest or render expedient, but such are intended to cover the application and\or implementation without departing from the spirit or scope of the claims.

What is claimed is:

1. A method, comprising:
   receiving, by a processor, patient information of a patient, the patient information comprising at least a patient identifier and a clinical episode associated with the patient;
   generating, by the processor, an episode card for the patient to avail health care services subsequently provided by one or more healthcare service providers for an eligibility period, the episode card comprising claims submission information for the healthcare services availed by the patient subsequently provided by the one or more healthcare service providers, wherein the episode card is used in lieu of the patient's regular insurance card for the clinical episode;
   receiving, by the processor, one or more claims associated with the patient from at least one health care service provider of the one or more health care service providers, each claim being associated with one or more health care services availed by the patient in the predefined time for the clinical episode using the episode card;
   processing, by the processor, the one or more claims for determining validity of each claim of the one or more claims based on a comparison of the one or more health care services associated with each claim with a set of episode definition parameters, wherein the set of episode definition parameters is predefined for the clinical episode and comprises information of at least valid diagnoses of the clinical episode, the clinical episode start, the clinical episode length, and at least one valid health care service provider of the one or more health care service providers; and
   upon processing the one or more claims, facilitating, by the processor, a payment amount for the one or more claims of the at least one health care service provider based on the validity of the set of episode definition parameters;
   wherein generating the episode card for the patient comprises:
   accessing, by the processor, eligibility information of the patient based on an eligibility file provided by an insurance service provider or an employer group, the eligibility file comprising health insurance details of the patient;
   determining, by the processor, an eligibility of the patient for a bundled payment of claims for the clinical episode based on the eligibility information; and
   upon determining the patient as an eligible candidate for the bundled payment of claims, calculating, by the processor, a patient responsibility and a total bundled claim for the clinical episode of the patient.

2. The method as claimed in claim 1, wherein calculating the patient responsibility comprises:
   accessing, by the processor, the eligibility information of the patient to determine if the bundled payment of claims is based on an employer group carve-out scheme or a health plan payor scheme; and
   upon determining the bundled payment of claims is based on the employer group carve-out scheme, determining, by the processor, the patient responsibility based on the eligibility information.

3. The method as claimed in claim 2, wherein upon determining if the bundled payment of claims is based on the health plan payor scheme comprises:
   sending, by the processor, a financial information request to the insurance service provider for accessing financial information associated with the patient, the financial information comprising a deductible amount, a copay amount, a coinsurance amount and an out of pocket (OOP) max amount; and
   upon receiving the financial information, determining, by the processor, the patient responsibility for the clinical episode based on the financial information.

4. The method as claimed in claim 1, wherein processing the one or more claims comprises:
   classifying, by the processor, the one or more claims as a valid claim or an invalid claim; and
   facilitating, by the processor, a notification for the patient and the at least one health care service provider related to the valid or the invalid claim, the notification comprising reasons for determining the valid or the invalid claim.

5. The method as claimed in claim 4, further comprising:
   upon determining the valid claim, accessing, by the processor, a contracted payment rate for payment of at least a part of the payment amount for the one or more health care services associated with the valid claim; and
   facilitating, by the processor, payment of the payment amount for the valid claim associated with the at least one health care service provider.

6. The method as claimed in claim 1, wherein the episode card comprises one or more of:
   the patient information;
   the claims submission information; and
   one or more terms and conditions for the bundled payment of claims.

7. The method as claimed in claim 1, wherein the eligibility file is at least one of: an EDI 834 file; and a CSV file.

8. A server system, comprising:
   a memory configured to store instructions; and
   a processor configured to execute the instructions stored in the memory and thereby cause the server system to perform:

receiving patient information of a patient, the patient information comprising at least a patient identifier and a clinical episode associated with the patient;

generating an episode card for the patient to avail health care services subsequently provided by one or more healthcare service providers for an eligibility period, the episode card comprising claims submission information for healthcare services availed by the patient subsequently provided by the one or more healthcare service providers;

receiving one or more claims associated with the patient from at least one health care service provider of the one or more health care service providers, each claim being associated with one or more health care services availed by the patient in the predefined time for the clinical episode using the episode card, wherein the episode card is used in lieu of the patient's regular insurance card for the clinical episode;

processing the one or more claims for determining validity of each claim of the one or more claims based on a comparison of the one or more health care services associated with each claim with a set of episode definition parameters, wherein the set of episode definition parameters is predefined for the clinical episode and comprises information of at least valid diagnoses of the clinical episode, the clinical episode start, the clinical episode length, and at least one valid health care service provider of the one or more health care service providers; and upon processing the one or more claims, facilitating a payment amount for the one or more claims of the at least one health care service provider based on the validity of the set of episode definition parameters;

wherein for generating the episode card for the patient, the server system is further caused to perform at least:

accessing eligibility information of the patient based on an eligibility file provided by an insurance service provider or an employer group, the eligibility file comprising health insurance details of the patient;

determining an eligibility of the patient for a bundled payment of claims for the clinical episode based on the eligibility information; and upon determining the patient as an eligible candidate for the bundled payment of claims, calculating a patient responsibility and a total bundled claim for the clinical episode of the patient.

9. The server system as claimed in claim 8, wherein for calculating the patient responsibility, the server system is further caused to perform at least:

accessing the eligibility information of the patient to determine if the bundled payment of claims is based on an employer group carve-out scheme or a health plan payor scheme; and upon determining the bundled payment of claims as based on an employer group carve-out scheme, determining the patient responsibility based on the eligibility information.

10. The server system as claimed in claim 9, wherein upon determining if the bundled payment of claims is based on the health plan payor scheme, the server system is further caused to perform at least:

sending a financial information request to the insurance service provider for accessing financial information associated with the patient, the financial information comprising a deductible amount, a copay amount, a coinsurance amount and an out of pocket (OOP) max amount; and upon receiving the financial information, determining the patient responsibility for the clinical episode based on the financial information.

11. The server system as claimed in claim 8, wherein for processing the one or more claims, the server system is further caused to perform at least:

classifying the one or more claims as a valid claim or an invalid claim; and facilitating a notification for the patient and the at least one health care service provider related to the valid or the invalid claim, the notification comprising reasons for determining the valid or the invalid claim.

12. The server system as claimed in claim 11, wherein the server system is further caused to perform at least:

upon determining the valid claim, accessing a contracted payment rate for payment of at least a part of the payment amount for the one or more health care services associated with the valid claim; and facilitating the payment of the payment amount for the valid claim associated with the at least one health care service provider.

13. The server system as claimed in claim 8, wherein the episode card comprises one or more of:

the patient information;
the claims submission information; and
one or more terms and conditions for the bundled payment of claims.

14. The server system as claimed in claim 8, wherein the eligibility file is at least one of:

an EDI 834 file; and a CSV file.

15. A method, comprising:

receiving, by a processor, patient information of a patient, the patient information comprising at least a patient identifier, a clinical episode associated with the patient, and a primary health insurance information associated with the patient;

accessing, by the processor, eligibility information of the patient based on an eligibility file provided by an insurance service provider or an employer group, the eligibility file comprising health insurance details of the patient;

determining, by the processor, an eligibility of the patient for a bundled payment of claims for the clinical episode based on the eligibility information;

upon determining the patient as an eligible candidate for the bundled payment of claims, generating, by the processor, an episode card for the patient to avail healthcare services subsequently provided by one or more healthcare service providers for an eligibility period, wherein the one or more healthcare service providers raise one or more claims for at least one health care service availed by the patient using the episode card, wherein the episode card is used in lieu of the patient's regular insurance card for the clinical episode;

processing, by the processor, the one or more claims for determining validity of each claim of the one or more claims based on a comparison of the one or more health care services associated with each claim with a set of episode definition parameters, wherein the set of episode definition parameters is predefined for the clinical episode and comprises information of at least valid diagnoses of the clinical episode, the clinical episode start, the clinical episode length, and at least one valid health care service provider of the one or more health care service providers;

upon processing the one or more claims, facilitating, by the processor, a payment amount for the one or more claims of the at least one health care service provider based on the validity of the set of episode definition parameters;

wherein generating the episode card for the patient comprises: calculating, by the processor, a patient responsibility and a total bundled claim for the clinical episode of the patient based on the primary health insurance information; and wherein calculating the patient responsibility comprises:

determining, by the processor, if a health plan scheme in the primary health insurance information is at least one of an employer group carve-out scheme or a health plan pay or scheme, wherein in the employer group carve-out scheme, the patient responsibility is determined based on the eligibility information; and in the health plan payor scheme, the patient responsibility is determined based on a financial information comprising a deductible amount, a copay amount, a coinsurance amount and an out of pocket (OOP) max amount accessed from the insurance service provider.

16. The method as claimed in claim 15, wherein processing the one or more claims comprises:

classifying, by the processor, the one or more claims as a valid claim or an invalid claim based on the episode definition parameters; and facilitating, by the processor, a notification for the patient and the at least one health care service provider related to the valid or the invalid claim, the notification comprising reasons for determining the valid or the invalid claim.

* * * * *